(12) United States Patent
Liu et al.

(10) Patent No.: US 9,518,073 B2
(45) Date of Patent: *Dec. 13, 2016

(54) SILOXANE COMPOUND AND PROCESS FOR PRODUCING THE SAME

(71) Applicant: MILLIKEN & COMPANY, Spartanburg, SC (US)

(72) Inventors: Yuzhou Liu, Boiling Springs, SC (US); Keith A. Keller, Spartanburg, SC (US); Michael E. Wilson, Middleburg, FL (US)

(73) Assignee: Milliken & Company, Spartanburg, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/244,252

(22) Filed: Apr. 3, 2014

(65) Prior Publication Data

US 2014/0309449 A1 Oct. 16, 2014

Related U.S. Application Data

(60) Provisional application No. 61/811,479, filed on Apr. 12, 2013.

(51) Int. Cl.
| | |
|---|---|
| *C07F 7/21* | (2006.01) |
| *C08G 77/04* | (2006.01) |
| *H01L 33/56* | (2010.01) |
| *H01L 23/29* | (2006.01) |
| *C08G 77/12* | (2006.01) |
| *C08K 5/5419* | (2006.01) |
| *C08K 5/55* | (2006.01) |

(52) U.S. Cl.
CPC ............ *C07F 7/21* (2013.01); *C08G 77/04* (2013.01); *H01L 23/296* (2013.01); *H01L 33/56* (2013.01); *C08G 77/12* (2013.01); *C08K 5/5419* (2013.01); *C08K 5/55* (2013.01); *H01L 2224/48091* (2013.01); *H01L 2224/48247* (2013.01)

(58) Field of Classification Search
USPC ................................ 556/460, 461
See application file for complete search history.

(56) References Cited

U.S. PATENT DOCUMENTS

| | | | |
|---|---|---|---|
| 3,297,632 A * | 1/1967 | Wu ............... | C08G 77/04 528/12 |
| 3,378,575 A | 4/1968 | Brown, Jr. | |
| 3,557,177 A | 1/1971 | Selin | |
| 3,590,064 A | 6/1971 | Lacefield | |
| 5,247,116 A | 9/1993 | Buese et al. | |
| 5,298,589 A | 3/1994 | Buese et al. | |
| 5,347,028 A | 9/1994 | Buese et al. | |
| 5,491,249 A | 2/1996 | Kostas | |
| 5,670,689 A | 9/1997 | Allandrieu et al. | |
| 6,593,500 B2 | 7/2003 | Priou et al. | |
| 7,064,173 B2 | 6/2006 | Rubinsztajn et al. | |
| 7,148,370 B1 | 12/2006 | Rubinsztajn et al. | |
| 7,388,065 B2 | 6/2008 | Kennedy et al. | |
| 2003/0139287 A1 | 7/2003 | Deforth et al. | |
| 2004/0127668 A1 | 7/2004 | Rubinsztajn et al. | |
| 2005/0033001 A1 | 2/2005 | Cella et al. | |
| 2006/0041098 A1 | 2/2006 | Kennedy et al. | |
| 2010/0179283 A1 | 7/2010 | Sueyoshi et al. | |
| 2011/0062846 A1 | 3/2011 | Song et al. | |
| 2013/0079539 A1 | 3/2013 | Wilson | |

FOREIGN PATENT DOCUMENTS

| | | |
|---|---|---|
| DE | 19619002 A1 | 11/1996 |
| GB | 2 301 108 A | 11/1996 |

OTHER PUBLICATIONS

Brown, Jr., "The Polycondensation of Phenylsilanetriol", *General Electric Research Laboratory*, Schenectady, New York 12301, May 18, 1965, p. 4317.
Chrusciel, J. et al., Dehydrocondensation of Organic Hydrosilanes With Silanols, Part I. Kinetics and Mechanism of the Reaction in Dimethylformamide. *Polish Journal of Chemistry*, vol. 57, 1983, pp. 113-120.
Chrusciel, J. et al., "Dehydrocondensation of Organic Hydrosilanes With Silanols, Part II. Effect of Siloxane Chain Length on the Reactivity of Si—H End-Groups. The Substitution Effect". *Polish Journal of Chemistry*, vol. 57, 1983, pp. 121-128.
Mukbaniani, O. et al., "Arylenecyclosiloxame-Dimethylsiloxane Copolymers", *Journal of Applied Polymer Science*, vol. 82, 2001, 3142-3148, 2001 John Wiley & Sons, Inc.
Mukbaniani, et al., "Poly(1,3-disila-1,3diphenyl-2-oxaindane)-diphenylsiloxane-poly(dimethylsiloxane) Block Copolymers", *Journal of Applied Polymer Science*, 2006, 3462-3467 (2006)vol. 101, Wiley Periodicals, Inc., Republic of Georgia.
Seki, et al., "Stereochemistry of the reaction of cis, trans, cis-2,4,6,8-tetraisocyanato-2,4,6,8-tetramethycyclotetrasiloxane with triphenylsilanol and 1,1,3,3-tetraphenyldisiloxane-1,3-diol", *Journal of Organometallic Chemistry*, 2011, pp. 846-851, Issue 696, ScienceDirect, Japan.
Seki, et al., "Synthesis and structure of ladder polymethylsilsesquioxanes from sila-functionalized cyclotetrasiloxanes", *Journal of Organometallic Chemistry*, 2010, pp. 1363-1369, Issue 695, ScienceDirect, Japan.
Unno, et al., "cis-trans-cis-Tetrabromotetramethylcyclotetrasiloxane: a Versatile Precursor of Ladder Silsesquioxanes", *The Chemical Society of Japan*, 2005, pp. 1105-1109, Bull. Chem. Soc. Jpn, 78, published on the web Jun. 6, 2005; DOI 10.1246/bcsj.78.1105.

(Continued)

*Primary Examiner* — Pancham Bakshi
(74) *Attorney, Agent, or Firm* — Robert M. Lanning

(57) ABSTRACT

A siloxane compound comprises a plurality of siloxane repeating units and at least a portion of the siloxane repeating units are cyclosiloxane repeating units conforming to a specified structure. A process for producing such siloxane compounds is also provided. A process and kit for producing a cross-linked silicone polymer using the described siloxane compounds is also provided. A light emitting diode (LED) comprises an encapsulant, and the encapsulant comprises a cross-linked silicone polymer produced from the described siloxane compounds.

16 Claims, 1 Drawing Sheet

(56) References Cited

OTHER PUBLICATIONS

Unno, et al., "Synthesis of laddersiloxanes by novel stereocontrolled approach", *Journal of Organometallic Chemistry*, 2007, pp. 307-312, ScienceDirect, vol. 692, Japan.

International Search Report of PCT/US2014/033749 filed on Apr. 11, 2014, 3 pages.

Written Opinion of the International Searching authority for PCT/US2014/033749 filed on Apr. 11, 2014, 5 pages.

Andrianov, et al., Synthesis of bis[organocyclotri(tetra,penta)siloxy]poly(dimethylsiloxanes), Izvestiya Akademii Nauk SSSR, Seriya Khimicheskaya; (8), 1835-41, 1979 (English translation 1697-1702, 1980).

\* cited by examiner

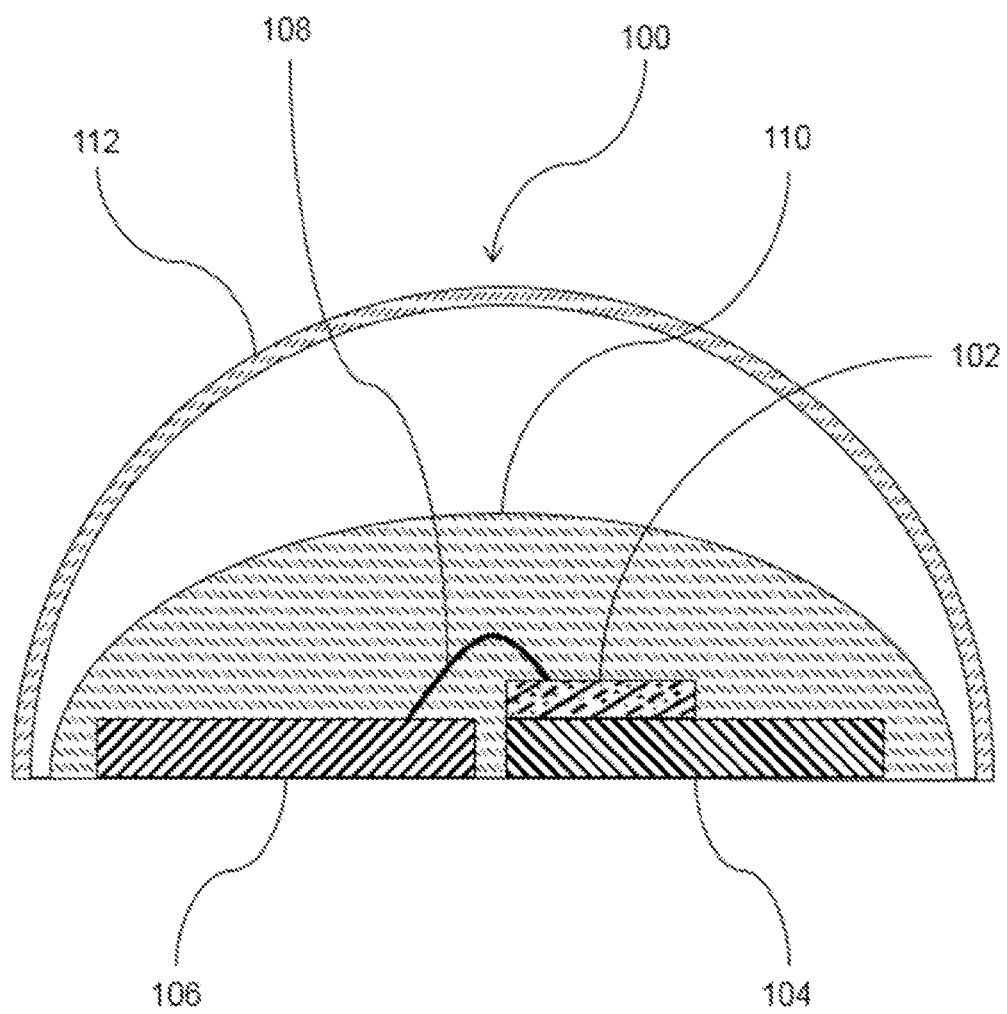

SILOXANE COMPOUND AND PROCESS FOR PRODUCING THE SAME

CROSS-REFERENCE TO RELATED APPLICATIONS

This application claims, pursuant to 35 U.S.C. §119(e), the benefit of the filing date of U.S. Patent Application No. 61/811,479, which was filed on Apr. 12, 2013.

TECHNICAL FIELD

This application relates to siloxane compounds (e.g., siloxane oligomers and siloxane compounds), cross-linked silicone polymers, and processes for the producing the same.

BACKGROUND

Siloxane compounds and silicones have found many uses in modern industry. For example, siloxane compounds are widely used in the production of cross-linked silicone polymers. These polymers typically are produced by either a hydrosilylation reaction or a condensation reaction. In the hydrosilylation reaction, siloxane compounds bearing vinyl groups undergo addition to link individual molecules of the compounds through the formation of new Si—C bonds. The hydrosilylation reaction typically is catalyzed by platinum, which contributes to the cost of these polymers because the platinum cannot be recovered from the cured elastomer. In the condensation reaction, the siloxane compounds react in a condensation reaction to form new Si—O—Si linkages between individual molecules. This condensation reaction produces volatile organic compounds (VOCs) as a by-product.

Cross-linked silicone polymers can be used as sealants or encapsulants for electronics. In particular, cross-linked silicone polymers can be used as encapsulants for light emitting diodies (LEDs). These cross-linked silicone polymers are desirable because they do not interfere with the operation of the electronic components. However, the cross-linked silicone polymers that exhibit sufficiently high temperature stability to be used as encapsulants for higher power LEDs do not have a high refractive index. This lower refractive index means that the light output from the LED will be reduced due to internal reflections in the semiconductor die of the LED.

A need remains for siloxane compounds that are suitable for use in making cross-linked silicone polymers without generating a large amount of volatile reaction products, such as the carbon-containing VOC's produced by condensation cure cross-linked silicone polymers. A need also remains for siloxane compounds and cross-linked silicone polymers that exhibit a high refractive index and are therefore better suited for use in those applications that demand an encapsulant material exhibiting a high refractive index (e.g., LED encapsulant applications). A need also remains for processes for generating these siloxane compounds and cross-linked silicone polymers. The subject matter described in the present application seeks to address these and other needs.

BRIEF SUMMARY OF THE INVENTION

In a first embodiment, the invention provides a siloxane compound comprising a plurality of siloxane repeating units, wherein about 10 mol. % or more of the siloxane repeating units are cyclotrisiloxane repeating units, and the cyclotrisiloxane repeating units are independently selected from the group consisting of cyclotrisiloxane repeating units conforming to the structure of Formula (I) below:

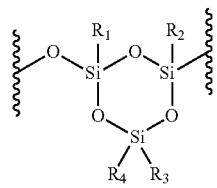

wherein $R_1$ and $R_2$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; $R_3$ and $R_4$ are independently selected from the group consisting of alkyl groups, substituted alkyl groups, alkanediyl groups, substituted alkanediyl groups, cycloalkyl groups, substituted cycloalkyl groups, alkenyl groups, substituted alkenyl groups, alkenediyl groups, substituted alkenediyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; provided, if one of $R_3$ and $R_4$ is selected from the group consisting of alkanediyl groups, substituted alkanediyl groups, alkenediyl groups, and substituted alkenediyl groups, then the other of $R_3$ and $R_4$ is also selected from the group consisting of alkanediyl groups, substituted alkanediyl groups, alkenediyl groups, and substituted alkenediyl groups, and $R_3$ and $R_4$ are bonded to form a cyclic moiety.

In a second embodiment, the invention provides a process for producing a siloxane compound, the process comprising the steps of:

(a) providing a first siloxane compound, the first siloxane compound comprising at least one segment conforming to the structure of Formula (XX)

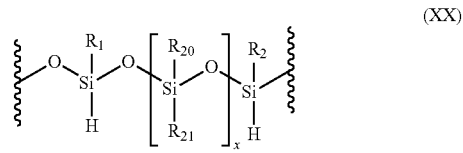

wherein $R_1$ and $R_2$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; $R_{20}$ and $R_{21}$ are independently selected from the group consisting of hydrogen, alkyl groups, substituted alkyl groups, alkanediyl groups, substituted alkanediyl groups, cycloalkyl groups, substituted cycloalkyl groups, alkenyl groups, substituted alkenyl groups, alkenediyl groups, substituted alkenediyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; provided only one of $R_{20}$ and $R_{21}$ can be hydrogen; and further provided, if one of $R_{20}$ and $R_{21}$ is selected from the group consisting of alkanediyl groups, substituted alkanediyl groups, alkenediyl groups, and substituted alkenediyl groups, then the other of $R_{20}$ and $R_{21}$ is also selected from the group consisting of alkanediyl groups, substituted alkanediyl groups, alkenediyl groups, and substituted alkenediyl groups, and $R_{20}$ and $R_{21}$ are bonded to form a cyclic moiety; x is 0 or any positive integer;

(b) providing an organosilicon compound conforming to the structure of Formula (XXX)

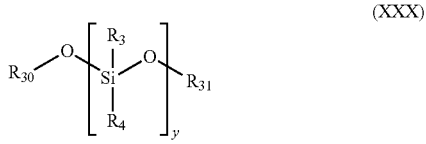
(XXX)

wherein $R_3$ and $R_4$ are independently selected from the group consisting of alkyl groups, substituted alkyl groups, alkanediyl groups, substituted alkanediyl groups, cycloalkyl groups, substituted cycloalkyl groups, alkenyl groups, substituted alkenyl groups, alkenediyl groups, substituted alkenediyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; provided, if one of $R_3$ and $R_4$ is selected from the group consisting of alkanediyl groups, substituted alkanediyl groups, alkenediyl groups, and substituted alkenediyl groups, then the other of $R_3$ and $R_4$ is also selected from the group consisting of alkanediyl groups, substituted alkanediyl groups, alkenediyl groups, and substituted alkenediyl groups, and $R_3$ and $R_4$ are bonded to form a cyclic moiety; $R_{30}$ and $R_{31}$ are independently selected from the group consisting of hydrogen, alkyl groups, substituted alkyl groups, acyl groups, and substituted acyl groups; and y is a positive integer from 1 to 6;

(c) providing a reaction phase comprising a Lewis acid catalyst and a solvent;

(d) combining the first siloxane compound and the organosilicon compound in the reaction phase under conditions so that the first siloxane compound and the organosilicon compound react in a condensation reaction to produce a second siloxane compound, the second siloxane compound comprising at least one segment conforming to the structure of Formula (XL)

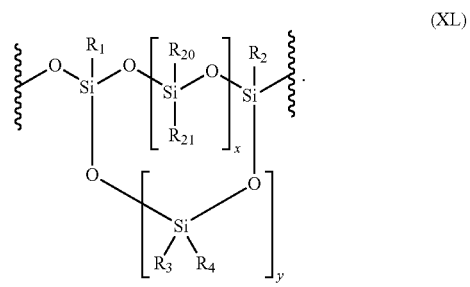
(XL)

In a third embodiment, the invention provides a siloxane compound comprising a plurality of siloxane repeating units, wherein at least a portion of the siloxane repeating units are cyclosiloxane repeating units, and the cyclosiloxane repeating units are independently selected from the group consisting of cyclosiloxane repeating units conforming to the structure of Formula (XL)

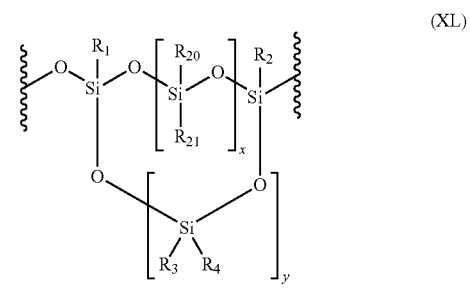
(XL)

wherein $R_1$ and $R_2$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; $R_{20}$ and $R_{21}$ are independently selected from the group consisting of hydrogen, alkyl groups, substituted alkyl groups, alkanediyl groups, substituted alkanediyl groups, cycloalkyl groups, substituted cycloalkyl groups, alkenyl groups, substituted alkenyl groups, alkenediyl groups, substituted alkenediyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; provided only one of $R_{20}$ and $R_{21}$ can be hydrogen; and further provided, if one of $R_{20}$ and $R_{21}$ is selected from the group consisting of alkanediyl groups, substituted alkanediyl groups, alkenediyl groups, and substituted alkenediyl groups, then the other of $R_{20}$ and $R_{21}$ is also selected from the group consisting of alkanediyl groups, substituted alkanediyl groups, alkenediyl groups, and substituted alkenediyl groups, and $R_{20}$ and $R_{21}$ are bonded to form a cyclic moiety; $R_3$ and $R_4$ are independently selected from the group consisting of haloalkyl groups, aralkyl groups, aryl groups, substituted aryl groups, heteroaryl groups, and substituted heteroaryl groups; x is 0 or any positive integer; and y is a positive integer from 1 to 6.

In a fourth embodiment, the invention provides a compound conforming to the structure of Formula (LXX)

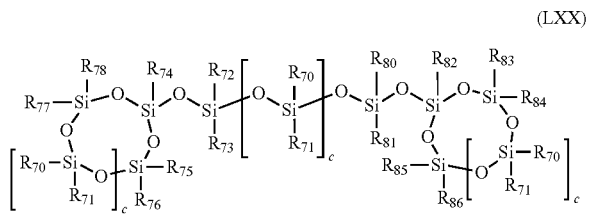

(LXX)

wherein $R_{70}$ and $R_{71}$ are independently selected from the group consisting of haloalkyl groups, aralkyl groups, aryl groups, substituted aryl groups, heteroaryl groups, and substituted heteroaryl groups; c is 0 or a positive integer from 1 to 3; $R_{72}$, $R_{73}$, $R_{74}$, $R_{75}$, $R_{76}$, $R_{77}$, $R_{78}$, $R_{80}$, $R_{81}$, $R_{82}$, $R_{83}$, $R_{84}$, $R_{85}$, and $R_{86}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; provided, if c is 0, then $R_{74}$ and $R_{82}$ are independently selected from the group consisting of haloalkyl groups, aralkyl groups, aryl groups, substituted aryl groups, heteroaryl groups, and substituted heteroaryl groups.

In a fifth embodiment, the invention provides a process for producing a cross-linked silicone polymer, the process comprising the steps of:

(a) providing a first siloxane compound, the first siloxane compound comprising a plurality of repeating units conforming to the structure of Formula (XL)

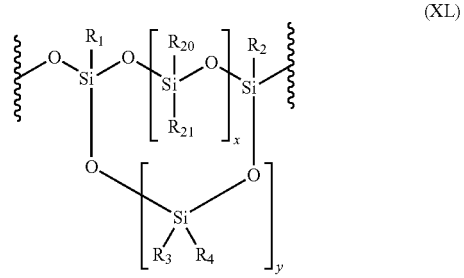

(XL)

wherein $R_1$ and $R_2$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiaryl-siloxy groups, and triarylsiloxy groups; $R_3$ and $R_4$ are independently selected from the group consisting of alkyl groups, substituted alkyl groups, alkanediyl groups, substituted alkanediyl groups, cycloalkyl groups, substituted cycloalkyl groups, alkenyl groups, substituted alkenyl groups, alkenediyl groups, substituted alkenediyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; provided, if one of $R_3$ and $R_4$ is selected from the group consisting of alkanediyl groups, substituted alkanediyl groups, alkenediyl groups, and substituted alkenediyl groups, then the other of $R_3$ and $R_4$ is also selected from the group consisting of alkanediyl groups, substituted alkanediyl groups, alkenediyl groups, and substituted alkenediyl groups, and $R_3$ and $R_4$ are bonded to form a cyclic moiety; $R_{20}$ and $R_{21}$ are independently selected from the group consisting of hydrogen, alkyl groups, substituted alkyl groups, alkanediyl groups, substituted alkanediyl groups, cycloalkyl groups, substituted cycloalkyl groups, alkenyl groups, substituted alkenyl groups, alkenediyl groups, substituted alkenediyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; provided only one of $R_{20}$ and $R_{21}$ can be hydrogen; and further provided, if one of $R_{20}$ and $R_{21}$ is selected from the group consisting of alkanediyl groups, substituted alkanediyl groups, alkenediyl groups, and substituted alkenediyl groups, then the other of $R_{20}$ and $R_{21}$ is also selected from the group consisting of alkanediyl groups, substituted alkanediyl groups, alkenediyl groups, and substituted alkenediyl groups, and $R_{20}$ and $R_{21}$ are bonded to form a cyclic moiety; x is 0 or a positive integer from 1 to 6; and y is a positive integer from 1 to 6;

(b) providing a ring-opening catalyst;
(c) combining the first siloxane compound and the ring-opening catalyst to produce a reaction mixture;
(d) reacting the components in the reaction mixture under conditions such that (i) the ring-opening catalyst opens at least a portion of the repeating units conforming to the structure of Formula (XL) in the first siloxane compound to form cross-linking groups and (ii) at least a portion of the cross-linking groups react with other molecules of the first siloxane compound to produce cross-links between molecules thereby forming a cross-linked silicone polymer.

In a sixth embodiment, the invention provides a kit for producing a cross-linked silicone polymer, the kit comprising a first part and a second part, the first part and second part being physically isolated from each other until such time as they are mixed to produce a cross-linked silicone polymer, wherein:

(a) the first part comprises a first siloxane compound, the first siloxane compound comprising a plurality of repeating units conforming to the structure of Formula (XL)

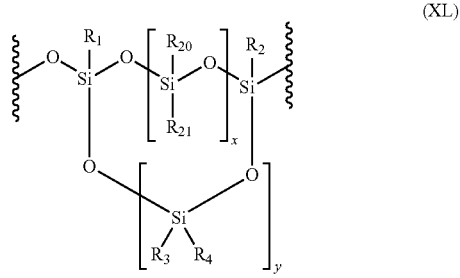

(XL)

wherein $R_1$ and $R_2$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; $R_3$ and $R_4$ are independently selected from the group consisting of alkyl groups, substituted alkyl groups, alkanediyl groups, substituted alkanediyl groups, cycloalkyl groups, substituted cycloalkyl groups, alkenyl groups, substituted alkenyl groups, alkenediyl groups, substituted alkenediyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; provided, if one of $R_3$ and $R_4$ is selected from the group consisting of alkanediyl groups, substituted alkanediyl groups, alkenediyl groups, and substituted alkenediyl groups, then the other of $R_3$ and $R_4$ is also selected from the group consisting of alkanediyl groups, substituted alkanediyl groups, alkenediyl groups, and substituted alkenediyl groups, and $R_3$ and $R_4$ are bonded to form a cyclic moiety; $R_{20}$ and $R_{21}$ are independently selected from the group consisting of hydrogen, alkyl groups, substituted alkyl groups, alkanediyl groups, substituted alkanediyl groups, cycloalkyl groups, substituted cycloalkyl groups, alkenyl groups, substituted alkenyl groups, alkenediyl groups, substituted alkenediyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; provided only one of $R_{20}$ and $R_{21}$ can be hydrogen; and further provided, if one of $R_{20}$ and $R_{21}$ is selected from the group consisting of alkanediyl groups, substituted alkanediyl groups, alkenediyl groups, and substituted alkenediyl groups, then the other of $R_{20}$ and $R_{21}$ is also selected from the group consisting of alkanediyl groups, substituted alkanediyl groups, alkenediyl groups, and substituted alkenediyl groups, and $R_{20}$ and $R_{21}$ are bonded to form a cyclic moiety; x is 0 or a positive integer from 1 to 6; and y is a positive integer from 1 to 6; and (b) the second part comprises a ring-opening catalyst.

In a seventh embodiment, the invention provides a light-emitting diode comprising:

(a) a semiconductor crystal, the semiconductor crystal comprising an n-type semiconductor material in a first region of the semiconductor crystal, a p-type semiconductor material in a second region of the semiconductor crystal, and a p-n junction at the boundary between the first region and the second region of the semiconductor material;

(b) a cathode electrically connected to the first region of the semiconductor crystal, (c) an anode electrically connected to the second region of the semiconductor crystal, and (d) an encapsulant material surrounding the semiconductor crystal, the encapsulant material comprising a cross-linked silicone polymer produced by a process comprising the steps of:

(i) providing a first siloxane compound, the first siloxane compound comprising a plurality of repeating units conforming to the structure of Formula (XL)

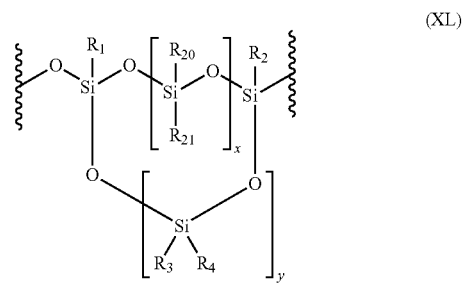

wherein $R_1$ and $R_2$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; $R_{20}$ and $R_{21}$ are independently selected from the group consisting of hydrogen, alkyl groups, substituted alkyl groups, alkanediyl groups, substituted alkanediyl groups, cycloalkyl groups, substituted cycloalkyl groups, alkenyl groups, substituted alkenyl groups, alkenediyl groups, substituted alkenediyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; provided only one of $R_{20}$ and $R_{21}$ can be hydrogen; and further provided, if one of $R_{20}$ and $R_{21}$ is selected from the group consisting of alkanediyl groups, substituted alkanediyl groups, alkenediyl groups, and substituted alkenediyl groups, then the other of $R_{20}$ and $R_{21}$ is also selected from the group consisting of alkanediyl groups, substituted alkanediyl groups, alkenediyl groups, and substituted alkenediyl groups, and $R_{20}$ and $R_{21}$ are bonded to form a cyclic moiety; x is 0 or a positive integer from 1 to 6; and y is a positive integer from 1 to 6;

(ii) providing a ring-opening catalyst;

(iii) combining the first siloxane compound and the ring-opening catalyst to produce a reaction mixture;

(iv) reacting the components in the reaction mixture under conditions such that (A) the ring-opening catalyst opens at least a portion of the repeating units conforming to the structure of Formula (XL) in the first siloxane compound to form cross-linking groups and (B) at least a portion of the cross-linking groups react with other molecules of the first siloxane compound to produce cross-links between molecules thereby forming a cross-linked silicone polymer.

BRIEF DESCRIPTION OF THE DRAWINGS

FIG. 1 is a schematic, cross-sectional representation of a light emitting diode (LED) according to the invention.

DETAILED DESCRIPTION OF THE INVENTION

The following definitions are provided to define several of the terms used throughout this application.

As used herein, the term "substituted alkyl groups" refers to univalent functional groups derived from substituted alkanes by removal of a hydrogen atom from a carbon atom of the alkane. In this definition, the term "substituted alkanes" refers to compounds derived from acyclic unbranched and branched hydrocarbons in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom (as in an ether) or a sulfur atom (as in a sulfide).

As used herein, the term "substituted cycloalkyl groups" refers to univalent functional groups derived from substituted cycloalkanes by removal of a hydrogen atom from a carbon atom of the cycloalkane. In this definition, the term "substituted cycloalkanes" refers to compounds derived from saturated monocyclic and polycyclic hydrocarbons (with or without side chains) in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom, a nitrogen atom, or a sulfur atom.

As used herein, the term "alkenyl groups" refers to univalent functional groups derived from acyclic, unbranched and branched olefins (i.e., hydrocarbons having one or more carbon-carbon double bonds) by removal of a hydrogen atom from a carbon atom of the olefin.

As used herein, the term "substituted alkenyl groups" refers to univalent functional groups derived from acyclic, substituted olefins by removal of a hydrogen atom from a carbon atom of the olefin. In this definition, the term "substituted olefins" refers to compounds derived from acyclic, unbranched and branched hydrocarbons having one or more carbon-carbon double bonds in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom (as in an ether) or a sulfur atom (as in a sulfide).

As used herein, the term "cycloalkenyl groups" refers to univalent functional groups derived from cyclic olefins (i.e., non-aromatic, monocyclic and polycyclic hydrocarbons having one or more carbon-carbon double bonds) by removal of a hydrogen atom from a carbon atom of the olefin. The carbon atoms in the cyclic olefins can be substituted with alkyl groups and/or alkenyl groups.

As used herein, the term "substituted cycloalkenyl groups" refers to univalent functional groups derived from substituted cyclic olefins by removal of a hydrogen atom from a carbon atom of the cyclic olefin. In this definition, the term "substituted cyclic olefins" refers to compounds derived from non-aromatic, monocyclic and polycyclic hydrocarbons having one or more carbon-carbon double bonds in which one or more of the hydrogen atoms of the hydrocarbon is replaced with a non-hydrogen atom (e.g., a halogen atom) or a non-alkyl functional group (e.g., hydroxy group, aryl group, heteroaryl group).

As used herein, the term "heterocyclyl groups" refers to univalent functional groups derived from heterocyclic compounds by removal of a hydrogen atom from an atom in the cyclic portion of the heterocyclic compound. In this definition, the term "heterocyclic compounds" refers to compounds derived from non-aromatic, monocyclic and polycyclic compounds having a ring structure composed of atoms of at least two different elements. These heterocyclic compounds can also comprise one or more double bonds.

As used herein, the term "substituted heterocyclyl groups" refers to univalent functional groups derived from substituted heterocyclic compounds by removal of a hydrogen atom from an atom in the cyclic portion of the compound. In this definition, the term "substituted heterocyclic compounds" refers to compounds derived from non-aromatic, monocyclic and polycyclic compounds having a ring structure composed of atoms of at least two different elements where one or more of the hydrogen atoms of the cyclic compound is replaced with a non-hydrogen atom (e.g., a halogen atom) or a functional group (e.g., hydroxy group, alkyl group, aryl group, heteroaryl group). These substituted heterocyclic compounds can also comprise one or more double bonds.

As used herein, the term "substituted aryl groups" refers to univalent functional groups derived from substituted arenes by removal of a hydrogen atom from a ring carbon atom. In this definition, the term "substituted arenes" refers to compounds derived from monocyclic and polycyclic aromatic hydrocarbons in which one or more of the hydrogen atoms of the hydrocarbon is replaced with a non-hydrogen atom (e.g., a halogen atom) or a non-alkyl functional group (e.g., hydroxy group).

As used herein, the term "substituted heteroaryl groups" refers to univalent functional groups derived from substituted heteroarenes by removal of a hydrogen atom from a ring carbon atom. In this definition, the term "substituted arenes" refers to compounds derived from monocyclic and polycyclic aromatic hydrocarbons in which (1) one or more of the hydrogen atoms of the hydrocarbon is replaced with a non-hydrogen atom (e.g., a halogen atom) or a non-alkyl functional group (e.g., hydroxy group) and (2) at least one methine group (—C=) of the hydrocarbon is replaced by a trivalent heteroatom and/or at least one vinylidene group (—CH=CH—) of the hydrocarbon is replaced by a divalent heteroatom.

As used herein, the term "alkanediyl groups" refers to divalent functional groups derived from alkanes by removal of two hydrogen atoms from the alkane. These hydrogen atoms can be removed from the same carbon atom on the alkane (as in ethane-1,1-diyl) or from different carbon atoms (as in ethane-1,2-diyl).

As used herein, the term "substituted alkanediyl groups" refers to divalent functional groups derived from substituted alkanes by removal of two hydrogen atoms from the alkane. These hydrogen atoms can be removed from the same carbon atom on the substituted alkane (as in 2-fluoroethane-1,1-diyl) or from different carbon atoms (as in 1-fluoroethane-1,2-diyl). In this definition, the term "substituted alkanes" has the same meaning as set forth above in the definition of substituted alkyl groups.

As used herein, the term "alkenediyl groups" refers to divalent functional groups derived from acyclic, unbranched and branched olefins (i.e., hydrocarbons having one or more carbon-carbon double bonds) by removal of two hydrogen atoms from the olefin. These hydrogen atoms can be removed from the same carbon atom on the olefin (as in but-2-ene-1,1-diyl) or from different carbon atoms (as in but-2-ene-1,4-diyl).

As used herein, the term "acyl groups" refers to univalent functional groups derived from alkyl carboxylic acids by removal of a hydroxy group from a carboxylic acid group. In this definition, the term "alkyl carboxylic acids" refers to acyclic, unbranched and branched hydrocarbons having one or more carboxylic acid groups.

As used herein, the term "substituted acyl groups" refers to univalent functional groups derived from substituted alkyl carboxylic acids by removal of a hydroxy group from a carboxylic acid group. In this definition, the term "substituted alkyl carboxylic acids" refers to compounds having one or more carboxylic acid groups bonded to a substituted alkane, and the term "substituted alkane" is defined as it is above in the definition of substituted alkyl groups.

In a first embodiment, the invention provides a siloxane compound comprising a plurality of siloxane repeating units. Preferably, at least some of the siloxane repeating units are cyclotrisiloxane repeating units, and these cyclotrisiloxane repeating units are independently selected from the group consisting of repeating units conforming to the structure of Formula (I) below:

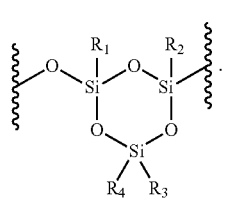

(I)

In the structure of Formula (I), $R_1$ and $R_2$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups. $R_3$ and $R_4$ are independently selected from the group consisting of alkyl groups, substituted alkyl groups, alkanediyl groups, substituted alkanediyl groups, cycloalkyl groups, substituted cycloalkyl groups, alkenyl groups, substituted alkenyl groups, alkenediyl groups, substituted alkenediyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups. $R_3$ and $R_4$ can also be bonded together to form a cyclic moiety. Thus, if one of $R_3$ and $R_4$ is selected from the group consisting of alkanediyl groups, substituted alkanediyl groups, alkenediyl groups, and substituted alkenediyl groups, then the other of $R_3$ and $R_4$ is also selected from the group consisting of alkanediyl groups, substituted alkanediyl groups, alkenediyl groups, and substituted alkenediyl groups, and $R_3$ and $R_4$ are bonded to form a cyclic moiety. $R_3$ and $R_4$ can also be bonded together to form a cyclic moiety. In the structure of Formula (I) and the structures that follow, the partial bonds (i.e., the bonds truncated by the wavy line) represent bonds to adjacent moieties or repeating units.

In a preferred embodiment, $R_1$ and $R_2$ are independently selected from the group consisting of $C_1$-$C_{30}$ alkyl groups (e.g., $C_1$-$C_8$ alkyl groups), $C_2$-$C_{30}$ alkenyl groups (e.g., $C_2$-$C_8$ alkenyl groups), $C_1$-$C_{30}$ haloalkyl groups (e.g., $C_1$-$C_8$ haloalkyl groups), $C_6$-$C_{30}$ aryl groups (e.g., $C_6$-$C_{10}$ aryl groups), $C_7$-$C_{31}$ aralkyl groups, $C_3$-$C_9$ trialkylsiloxy groups, $C_8$-$C_{26}$ aryldialkylsiloxy groups, $C_{13}$-$C_{28}$ alkyldiarylsiloxy groups, and $C_{18}$-$C_{30}$ triarylsiloxy groups. More preferably, $R_1$ and $R_2$ are independently selected from the group consisting of $C_1$-$C_8$ alkyl groups, $C_1$-$C_8$ haloalkyl groups, $C_6$-$C_{10}$ aryl groups, and $C_7$-$C_{31}$ aralkyl groups. Most preferably, $R_1$ and $R_2$ are independently selected from the group consisting of $C_1$-$C_8$ alkyl groups (e.g., methyl groups).

In a preferred embodiment, $R_3$ and $R_4$ are independently selected from the group consisting of $C_1$-$C_{30}$ alkyl groups (e.g., $C_1$-$C_8$ alkyl groups), $C_1$-$C_5$ alkanediyl groups, $C_2$-$C_{30}$ alkenyl groups (e.g., $C_2$-$C_8$ alkenyl groups), $C_2$-$C_5$ alkenediyl groups, $C_1$-$C_{30}$ haloalkyl groups (e.g., $C_1$-$C_8$ haloalkyl groups), $C_6$-$C_{30}$ aryl groups (e.g., $C_6$-$C_{10}$ aryl groups), $C_7$-$C_{31}$ aralkyl groups, $C_3$-$C_9$ trialkylsiloxy groups, $C_8$-$C_{26}$ aryldialkylsiloxy groups, $C_{13}$-$C_{28}$ alkyldiarylsiloxy groups, and $C_{18}$-$C_{30}$ triarylsiloxy groups. More preferably, $R_3$ and $R_4$ are independently selected from the group consisting of $C_1$-$C_8$ alkyl groups, $C_1$-$C_8$ haloalkyl groups, $C_6$-$C_{10}$ aryl groups, and $C_7$-$C_{31}$ aralkyl groups. More preferably, $R_3$ and $R_4$ are independently selected from the group consisting of $C_6$-$C_{10}$ aryl groups. Most preferably, $R_3$ and $R_4$ are each phenyl groups.

The siloxane compound of this first embodiment can comprise any suitable amount of siloxane repeating units conforming to the structure of Formula (I). Preferably, about 10 mol. % or more of the siloxane repeating units in the compound conform to the structure of Formula (I). More preferably, about 15 mol. % or more, about 20 mol. % or more, about 25 mol. % or more, about 30 mol. % or more, about 35 mol. % or more, about 40 mol. % or more, about 45 mol. % or more, about 50 mol. % or more, about 55 mol. % or more, about 60 mol. % or more, about 65 mol. % or more, about 70 mol. % or more, about 75 mol. % or more, about 80 mol. % or more, about 85 mol. % or more, or about 90 mol. % or more of the siloxane repeating units in the compound conform to the structure of Formula (I).

The percentage of siloxane repeating units possessing the recited structure can be determined by any suitable analytical technique. For example, the relative amount of silicon atoms in a particular repeating unit can be quantified using $^{29}$Si nuclear magnetic resonance (NMR). The chemical shift of a silicon atom varies depending upon the particular moiety or repeating unit within which the silicon atom resides. Thus, using the NMR spectrum of the siloxane compound, one can determine the different types of silicon-containing moieties or repeating units present in the compound. Furthermore, when the area under each peak in the NMR spectrum is calculated, these area figures can be used to determine the relative amount of silicon atoms present in each different type of siloxane moiety or repeating unit.

The cyclotrisiloxane repeating units present in the siloxane compound of this first embodiment possess the same basic structure (i.e., a structure conforming to Formula (I)), but all of the repeating units are not necessarily substituted with the same groups. In other words, a siloxane compound according to this first embodiment of the invention can contain cyclotrisiloxane repeating units that differ in the selection of the $R_1$, $R_2$, $R_3$, and $R_4$ substituents.

As noted above, the siloxane compound of this first embodiment can comprise siloxane units in addition to those conforming to the structure of Formula (I). For example, in a preferred embodiment, the siloxane compound can comprise one or more segments conforming to the structure of Formula (X) below:

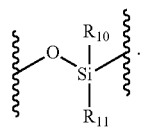

(X)

In the structure of Formula (X), $R_{10}$ and $R_{11}$ are independently selected from the group consisting of hydrogen, alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups. In the structure of Formula (X), only one of $R_{10}$ and $R_{11}$ can be hydrogen. More preferably, $R_{10}$ and $R_{11}$ are independently selected from the group consisting of $C_1$-$C_{30}$ alkyl groups (e.g., $C_1$-$C_8$ alkyl groups), $C_2$-$C_{30}$ alkenyl groups (e.g., $C_2$-$C_8$ alkenyl groups), $C_1$-$C_{30}$ haloalkyl groups (e.g., $C_1$-$C_8$ haloalkyl groups), $C_6$-$C_{30}$ aryl groups (e.g., $C_6$-$C_{10}$ aryl groups), $C_7$-$C_{31}$ aralkyl groups, $C_3$-$C_9$ trialkylsiloxy groups, $C_8$-$C_{26}$ aryldialkylsiloxy groups, $C_{13}$-$C_{28}$ alkyldiarylsiloxy groups, and $C_{18}$-$C_{30}$ triarylsiloxy groups. More preferably, $R_{10}$ and $R_{11}$ are independently selected from the group consisting of $C_1$-$C_8$ alkyl groups, $C_1$-$C_8$ haloalkyl groups, $C_6$-$C_{10}$ aryl groups, and $C_7$-$C_{31}$ aralkyl groups. Most preferably, $R_{10}$ and $R_{11}$ are independently selected from the group consisting of $C_1$-$C_8$ alkyl groups (e.g., methyl groups).

In another preferred embodiment, the siloxane compound of the first embodiment further comprises at least one segment conforming to the structure of Formula (XV) or Formula (XL) described below. The structure of Formula (XV) is

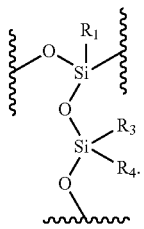

(XV)

In this structure, $R_1$, $R_3$, and $R_4$ are selected from the groups described above. The structure of Formula (XL) is

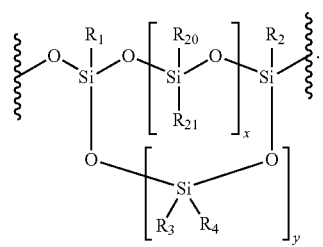

(XL)

In the structure of Formula (XL), $R_1$, $R_2$, $R_3$ and $R_4$ are selected from the groups described above, and $R_{20}$ and $R_{21}$ are independently selected from the group consisting of hydrogen, alkyl groups, substituted alkyl groups, alkanediyl groups, substituted alkanediyl groups, cycloalkyl groups, substituted cycloalkyl groups, alkenyl groups, substituted alkenyl groups, alkenediyl groups, substituted alkenediyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups. In the structure of (XL), only one of $R_{20}$ and $R_{21}$ can be hydrogen. Further, if one of $R_{20}$ and $R_{21}$ is selected from the group consisting of alkanediyl groups, substituted alkanediyl groups, alkenediyl groups, and substituted alkenediyl groups, then the other of $R_{20}$ and $R_{21}$ is also selected from the group consisting of alkanediyl groups, substituted alkanediyl groups, alkenediyl groups, and substituted alkenediyl groups, and $R_{20}$ and $R_{21}$ are bonded to form a cyclic moiety. The variable x is 0 or any positive integer; y is a positive integer from 1 to 6; and the sum of x and y is 2 or greater. In a preferred embodiment, x is selected from the group consisting of 0, 1, and 2; y is a positive integer from 1 to 6; and the sum of x and y is an integer from 2 to 8. In a more preferred embodiment, x is 1, and y is 1.

In a preferred embodiment of the structure of Formula (XL), $R_{20}$ is selected from the group consisting of $C_1$-$C_{30}$ alkyl groups (e.g., $C_1$-$C_8$ alkyl groups), $C_2$-$C_{30}$ alkenyl groups (e.g., $C_2$-$C_8$ alkenyl groups), $C_1$-$C_{30}$ haloalkyl groups (e.g., $C_1$-$C_8$ haloalkyl groups), $C_6$-$C_{30}$ aryl groups (e.g., $C_6$-$C_{10}$ aryl groups), $C_7$-$C_{31}$ aralkyl groups, $C_3$-$C_9$ trialkylsiloxy groups, $C_8$-$C_{26}$ aryldialkylsiloxy groups, $C_{13}$-$C_{28}$ alkyldiarylsiloxy groups, and $C_{18}C_{30}$ triarylsiloxy groups. More preferably, $R_{20}$ is selected from the group consisting of $C_1$-$C_8$ alkyl groups, $C_1$-$C_8$ haloalkyl groups, $C_6$-$C_{10}$ aryl groups, and $C_7$-$C_{31}$ aralkyl groups. In one particularly preferred embodiment, $R_{20}$ is selected from the group consisting of $C_1$-$C_8$ alkyl groups (e.g., a methyl group). In another particularly preferred embodiment, at least one of $R_{20}$ and $R_{21}$ is selected from the group consisting of $C_6$-$C_{30}$ aryl groups (e.g., $C_6$-$C_{10}$ aryl groups) and $C_7$-$C_{31}$ aralkyl groups, with a $C_6$-$C_{10}$ aryl group being more preferred and a phenyl group being most preferred.

In another preferred embodiment, $R_{21}$ is selected from the group consisting of hydrogen, $C_1$-$C_{30}$ alkyl groups (e.g., $C_1$-$C_8$ alkyl groups), $C_2$-$C_{30}$ alkenyl groups (e.g., $C_2$-$C_8$ alkenyl groups), $C_1$-$C_{30}$ haloalkyl groups (e.g., $C_1$-$C_8$ haloalkyl groups), $C_6$-$C_{30}$ aryl groups (e.g., $C_6$-$C_{10}$ aryl groups), $C_7$-$C_{31}$ aralkyl groups, $C_3$-$C_9$ trialkylsiloxy groups, $C_8$-$C_{26}$ aryldialkylsiloxy groups, $C_{13}$-$C_{28}$ alkyldiarylsiloxy groups, and $C_{18}$-$C_{30}$ triarylsiloxy groups. More preferably, $R_{21}$ is selected from the group consisting of hydrogen, $C_1$-$C_8$ alkyl groups, $C_1$-$C_8$ haloalkyl groups, $C_6$-$C_{10}$ aryl groups, and $C_7$-$C_{31}$ aralkyl groups. Most preferably, $R_{21}$ is selected from the group consisting of $C_1$-$C_8$ alkyl groups (e.g., a methyl group).

The structures drawn above only represent repeating units within the siloxane compound. The siloxane compound further comprises terminating groups. These terminating groups can be any suitable terminating group for a siloxane compound. In a preferred embodiment, the siloxane compound further comprises silyl terminating groups. Suitable silyl terminating groups include, but are not limited to, trialkylsilyl groups, such as trimethylsilyl groups.

In another preferred embodiment, the siloxane compound can comprise one or more cyclosiloxane terminating groups.

Preferably, the cyclosiloxane terminating group(s) conform to a structure selected from the group consisting of Formula (XLV) and Formula (XLVI)

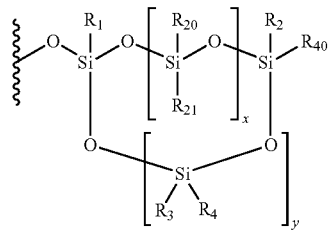

(XLV)

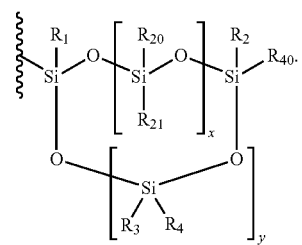

(XLVI)

In the structures of Formula (XLV) and Formula (XLVI), $R_1$, $R_2$, $R_3$, $R_4$, $R_{20}$, and $R_{21}$ are selected from the groups described above, and $R_{40}$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups. The variable x is 0 or any positive integer; and y is a positive integer from 1 to 6. In a preferred embodiment, x is selected from the group consisting of 0, 1, and 2; y is a positive integer from 1 to 6; and the sum of x and y is an integer from 1 to 8. In a particularly preferred embodiment of such a cyclosiloxane terminating group, x is 0 and y is 1.

In a preferred embodiment, $R_{40}$ is selected from the group consisting of $C_1$-$C_{30}$ alkyl groups (e.g., $C_1$-$C_8$ alkyl groups), $C_2$-$C_{30}$ alkenyl groups (e.g., $C_2$-$C_8$ alkenyl groups), $C_1$-$C_{30}$ haloalkyl groups (e.g., $C_1$-$C_8$ haloalkyl groups), $C_6$-$C_{30}$ aryl groups (e.g., $C_6$-$C_{10}$ aryl groups), $C_7$-$C_{31}$ aralkyl groups, $C_3$-$C_9$ trialkylsiloxy groups, $C_8$-$C_{26}$ aryldialkylsiloxy groups, $C_{13}$-$C_{28}$ alkyldiarylsiloxy groups, and $C_{18}$-$C_{30}$ triarylsiloxy groups. More preferably, $R_{40}$ is selected from the group consisting of $C_1$-$C_8$ alkyl groups, $C_1$-$C_8$ haloalkyl groups, $C_6$-$C_{10}$ aryl groups, and $C_7$-$C_{31}$ aralkyl groups. Most preferably, $R_{40}$ is independently selected from the group consisting of $C_1$-$C_8$ alkyl groups (e.g., methyl groups).

The siloxane compound of the first embodiment can have any suitable molecular weight. Preferably, the siloxane compound has a molecular weight of about 500 mol/g or more. In a preferred embodiment, the siloxane compound has molecular weight of about 500,000 mol/g or less.

The siloxane compound of the first embodiment preferably is optically transparent in at least the visible spectrum. The siloxane compound also preferably exhibits good stability (e.g., good thermal stability) and good solubility in a variety of organic solvents, such as toluene, xylene, tetrahydrofuran, dichloromethane, and acetonitrile.

The siloxane compound of this first embodiment can be produced by any suitable process. For example, the siloxane compound can be produced by dehydrogenative coupling of a hydrosilane and a hydroxysilane in the presence of a suitable catalyst, such as a platinum or ruthenium catalyst. However, in a second embodiment, the invention provides a process for producing siloxane compounds containing cyclosiloxane repeating units, such as the siloxane compound of the first embodiment. In particular, the process comprises the steps of: (a) providing a first siloxane compound; (b) providing an organosilicon compound; (c) providing a reaction phase comprising a Lewis acid catalyst and a solvent; and (d) combining the first siloxane compound and the organosilicon compound in the reaction phase under conditions so that the first siloxane compound and the organosilicon compound react in a condensation reaction to produce a second siloxane compound.

The first siloxane compound used in the process preferably comprises at least one segment conforming to the structure of Formula (XX)

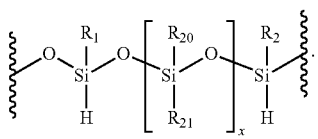

(XX)

In the structure of Formula (XX), $R_1$, $R_2$, $R_{20}$, and $R_{21}$ are selected from the various groups described above.

The first siloxane compound used in the process can comprise any suitable terminating groups. For example, the first siloxane compound can comprise silyl terminating groups, such as those discussed above in connection with the siloxane compound of the first embodiment of the invention. The first siloxane compound can also comprise hydride-bearing terminating groups. If such hydride-bearing terminating groups are present in the first siloxane compound, the siloxane compound produced by the process will contain some cyclosiloxane terminating groups, such as the cyclosiloxane terminating groups conforming to Formula (XLV) and Formula (XLVI) described above.

The organosilicon compound used in the process preferably conforms to the structure of Formula (XXX)

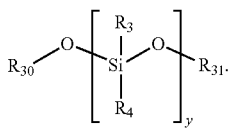

(XXX)

In the structure of (XXX), $R_3$ and $R_4$ are selected from the various groups described above, and $R_{30}$ and $R_{31}$ are independently selected from the group consisting of hydrogen, alkyl groups, substituted alkyl groups, acyl groups, and substituted acyl groups. Preferably, $R_{30}$ and $R_{31}$ are independently selected from the group consisting of hydrogen, $C_1$-$C_{30}$ alkyl groups (e.g., $C_1$-$C_8$ alkyl groups or $C_1$-$C_4$ alkyl groups), and $C_1$-$C_{30}$ acyl groups (e.g., $C_1$-$C_8$ acyl groups). Most preferably, $R_{30}$ and $R_{31}$ are each hydrogen. The variable y is a positive integer, preferably a positive integer from 1 to 6, and most preferably y is 1.

The first siloxane compound and the organosilicon compound are combined in a reaction phase comprising a Lewis acid catalyst and a solvent. The reaction phase can comprise any inert solvent that does not promote reaction other than condensation of the SiH functionality of the first siloxane compound with the SiOR functionality of the organosilicon compound, including undesired side reactions of these functionalities or of the siloxane bonds. Solvents comprising hydroxyl groups generally are inappropriate as solvents for the reaction phase. Depending on the identity of the substituents on the first siloxane compound and the organosilicon compound, the desired solvent can vary. Solvents that can be employed independently or as a mixture include, but are not limited to, aliphatic hydrocarbons (e.g., cyclohexane, heptane, or isooctane), aromatic hydrocarbons (e.g., toluene or xylenes), and siloxanes (e.g., hexamethyldisiloxane, octamethylcyclotetrasiloxane, or other cyclosiloxanes).

The reaction phase can comprise any suitable Lewis acid catalyst. In a preferred embodiment, the Lewis acid comprises a triphenylborane having the formula $B(C_6H_xX_{5-x})_3$, where x is 0 to 5 and X is independently F, $OCF_3$, $SCF_3$, R, or OR where R is H, $C_1$-$C_{22}$ alkyl or $C_6$-$C_{22}$ aryl. Other catalysts that can be employed are those disclosed in Priou et al. U.S. Pat. No. 6,593,500 and Deforth et al. U.S. Patent Application Publication No. 2003/0139287, which are incorporated herein by reference. The Lewis acid catalysts can be further modified to inhibit its miscibility in a non-reactive phase of the reaction mixture. For example, the Lewis acid catalyst can be attached to a resin where there is little or no affinity of the unreactive phase for the surface of the resin.

The first siloxane compound and the organosilicon compound are combined in the reaction phase so that they react in a condensation reaction to form a cyclosiloxane moiety conforming to the structure of Formula (XL) and yield the second siloxane compound. The formation of the cyclosiloxane moiety begins with a condensation reaction between an SiH functionality on the first siloxane compound with an SiOR functionality on the organosilicon compound. The cyclosiloxane moiety is completed when a remaining SiOR functionality on the molecule resulting from this initial reaction undergoes a condensation reaction with another SiH functionality on the same molecule. As will be understood by those skilled in the art, the subsequent reaction required to create the cyclosiloxane moiety also competes with other reactions that will not lead to the formation of a cyclosiloxane moiety. For example, the remaining SiOR functionality on the molecule resulting from the initial reaction could also undergo a condensation reaction with an SiH functionality on another molecule of the first siloxane compound. The result of such an intermolecular reaction will be a linking moiety conforming to the structure of Formula (XV), where the partial bond closest to the silicon atom bearing the $R_3$ and $R_4$ groups represents a bond to a silicon atom in a moiety derived from another molecule of the first siloxane compound. Thus, the reaction should be performed under conditions that are designed to promote the cyclo-condensation reaction over other competing intermolecular reactions. This can generally be accomplished by using a quasi-dilute system. A quasi-dilute system, as employed herein, is one where the products and one or more reagents can be in a high concentration in the reaction vessel, but in the reaction phase, the reactive functionalities are in sufficiently low concentrations—often very low concentrations depending on the desired size of the cyclosiloxane moiety and the nature of its substituents—that the second intramolecular reaction needed to form the cyclosiloxane moiety is very rapid relative to any intermolecular reaction.

The reaction can be performed at any suitable temperature. The reaction temperature can vary over a large range, from 0° C. or lower to temperatures in excess of 100° C. or even 200° C., depending upon the reagents, catalysts and solvents used, as can be appreciated and readily determined by one skilled in the art.

Once the reaction is complete, the catalyst preferably is removed from the product or deactivated in order to stabilize the product. It is believed that residual "active" catalyst in the product may cause the cyclosiloxane rings to open and begin to form cross-links in the product as described below. The catalyst can be removed from the product by adsorbing the catalyst on a suitable adsorbent, such as aluminum oxide, and then filtering the product to remove the adsorbent. The catalyst can be deactivated by adding any suitable Lewis base, such as an amine, phosphine, or phosphite, to the product.

In a third embodiment, the invention provides a siloxane compound comprising a plurality of siloxane repeating units. Preferably, at least a portion of the siloxane repeating units are cyclosiloxane repeating units, and the cyclosiloxane repeating units are independently selected from the group consisting of cyclosiloxane repeating units conforming to the structure of Formula (XL) below

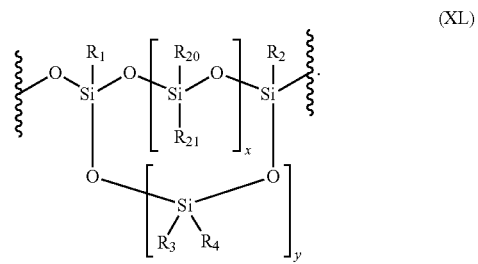

(XL)

In the structure of Formula (XL), $R_1$, $R_2$, $R_{20}$, and $R_{21}$ are selected from the groups described above for the first embodiment of the invention. The variable x is 0 or any positive integer; and y is a positive integer from 1 to 6. In a preferred embodiment, x is selected from the group consisting of 0, 1, and 2; y is a positive integer from 1 to 6; and the sum of x and y is an integer from 1 to 8. In a particularly preferred embodiment, at least a portion of the repeating units have a structure in which x is 0 and y is 1. In the structure of Formula (XL), $R_3$ and $R_4$ are independently selected from the group consisting of haloalkyl groups, aralkyl groups, aryl groups, substituted aryl groups, heteroaryl groups, and substituted heteroaryl groups. In a preferred embodiment, $R_3$ and $R_4$ are independently selected from the group consisting of $C_1$-$C_{30}$ haloalkyl groups (e.g., $C_1$-$C_8$ haloalkyl groups), $C_7$-$C_{31}$ aralkyl groups, $C_6$-$C_{30}$ aryl groups (e.g., $C_6$-$C_{10}$ aryl groups), and $C_6$-$C_{30}$ substituted aryl groups (e.g., $C_6$-$C_{10}$ substituted aryl groups). More preferably, $R_3$ and $R_4$ are independently selected from the group consisting of $C_1$-$C_8$ haloalkyl groups, $C_6$-$C_{10}$ aryl groups, and $C_6$-$C_{10}$ substituted aryl groups. In one preferred embodiment, $R_3$ and $R_4$ are independently selected from the group consisting of $C_6$-$C_{10}$ aryl groups, with phenyl groups being particularly preferred. In another preferred embodiment, $R_3$ and $R_4$ are independently selected from the group consisting of haloalkyl groups (e.g., $C_1$-$C_8$ haloalkyl groups), with fluoroalkyl groups (e.g., $C_1$-$C_8$ fluoroalkyl groups) being particularly preferred.

As with the siloxane compound of the first embodiment, the siloxane compound of this third embodiment can further comprise one or more segments conforming to the structure of Formula (X) described above. The siloxane compound of this third embodiment can also comprise one or more segments conforming to the structure of Formula (XV) described above. The siloxane compound can also comprise any suitable terminating groups, such as the various terminating groups described above in connection with the first embodiment of the invention.

The siloxane compound of this third embodiment can be produced by any suitable process, including the process described above in connection with the second embodiment of the invention.

In a fourth embodiment, the invention provides a siloxane compound conforming to the structure of Formula (LXX) below

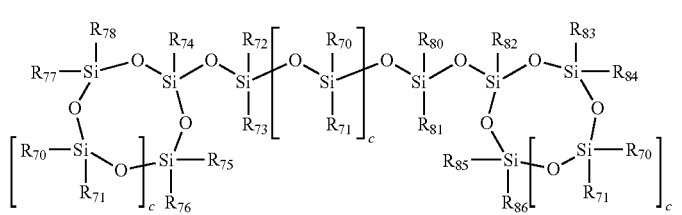

(LXX)

In the structure of Formula (LXX), $R_{70}$ and $R_{71}$ are independently selected from the group consisting of haloalkyl groups, aralkyl groups, aryl groups, substituted aryl groups, heteroaryl groups, and substituted heteroaryl groups. The variable c is 0 or a positive integer from 1 to 3. $R_{72}$, $R_{73}$, $R_{74}$, $R_{75}$, $R_{76}$, $R_{77}$, $R_{78}$, $R_{80}$, $R_{81}$, $R_{82}$, $R_{83}$, $R_{84}$, $R_{85}$, and $R_{86}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups. If c is 0, then $R_{74}$ and $R_{82}$ are independently selected from the group consisting of haloalkyl groups, aralkyl groups, aryl groups, substituted aryl groups, heteroaryl groups, and substituted heteroaryl groups.

In a preferred embodiment, $R_{70}$ and $R_{71}$ are independently selected from the group consisting of $C_1$-$C_{30}$ haloalkyl groups (e.g., $C_1$-$C_8$ haloalkyl groups), $C_7$-$C_{31}$ aralkyl groups, $C_6$-$C_{30}$ aryl groups (e.g., $C_6$-$C_{10}$ aryl groups), and $C_6$-$C_{30}$ substituted aryl groups (e.g., $C_6$-$C_{10}$ substituted aryl groups). More preferably, $R_{70}$ and $R_{71}$ are independently selected from the group consisting of $C_1$-$C_8$ haloalkyl groups, $C_6$-$C_{10}$ aryl groups, and $C_6$-$C_{10}$ substituted aryl groups. In one preferred embodiment, $R_{70}$ and $R_{71}$ are independently selected from the group consisting of $C_6$-$C_{10}$ aryl groups, with phenyl groups being particularly preferred. In another preferred embodiment, $R_{70}$ and $R_{71}$ are independently selected from the group consisting of haloalkyl groups (e.g., $C_1$-$C_8$ haloalkyl groups), with fluoroalkyl groups (e.g., $C_1$-$C_8$ fluoroalkyl groups) being particularly preferred.

In a preferred embodiment, $R_{72}$, $R_{73}$, $R_{74}$, $R_{75}$, $R_{76}$, $R_{77}$, $R_{78}$, $R_{80}$, $R_{81}$, $R_{82}$, $R_{83}$, $R_{84}$, $R_{85}$, and $R_{86}$ are independently selected from the group consisting of $C_1$-$C_{30}$ alkyl groups (e.g., $C_1$-$C_8$ alkyl groups), $C_2$-$C_{30}$ alkenyl groups (e.g., $C_2$-$C_8$ alkenyl groups), $C_1$-$C_{30}$ haloalkyl groups (e.g., $C_1$-$C_8$ haloalkyl groups), $C_6$-$C_{30}$ aryl groups (e.g., $C_6$-$C_{10}$ aryl groups), $C_7$-$C_{31}$ aralkyl groups, $C_3$-$C_9$ trialkylsiloxy groups, $C_8$-$C_{26}$ aryldialkylsiloxy groups, $C_{13}$-$C_{28}$ alkyldiarylsiloxy groups, and $C_{18}$-$C_{30}$ triarylsiloxy groups. More preferably, $R_{72}$, $R_{73}$, $R_{74}$, $R_{75}$, $R_{76}$, $R_{77}$, $R_{78}$, $R_{80}$, $R_{81}$, $R_{82}$, $R_{83}$, $R_{84}$, $R_{85}$, and $R_{86}$ are independently selected from the group consisting of alkyl groups (e.g., $C_1$-$C_8$ alkyl groups), haloalkyl groups (e.g., $C_1$-$C_8$ haloalkyl groups), aryl groups (e.g., $C_6$-$C_{30}$ aryl groups), and aralkyl groups (e.g., $C_7$-$C_{31}$ aralkyl groups). Most preferably, $R_{72}$, $R_{73}$, $R_{75}$, $R_{76}$, $R_{77}$, $R_{78}$, $R_{80}$, $R_{81}$, $R_{83}$, $R_{84}$, $R_{85}$, and $R_{86}$ are independently selected from the group consisting of alkyl groups (e.g., $C_1$-$C_8$ alkyl groups, preferably methyl groups), and $R_{74}$ and $R_{82}$ are independently selected from the group consisting of aryl groups (e.g., $C_6$-$C_{30}$ aryl groups, $C_6$-$C_{10}$ aryl groups, preferably a phenyl group).

In a preferred embodiment of a compound according to Formula (LXX) in which c is 0, $R_{72}$, $R_{73}$, $R_{75}$, $R_{76}$, $R_{77}$, $R_{78}$, $R_{80}$, $R_{81}$, $R_{83}$, $R_{84}$, $R_{85}$, and $R_{86}$ are independently selected from the group consisting of $C_1$-$C_{30}$ alkyl groups (e.g., $C_1$-$C_8$ alkyl groups), $C_2$-$C_{30}$ alkenyl groups (e.g., $C_2$-$C_8$ alkenyl groups), $C_1$-$C_{30}$ haloalkyl groups (e.g., $C_1$-$C_8$ haloalkyl groups), $C_6$-$C_{30}$ aryl groups (e.g., $C_6$-$C_{10}$ aryl groups), $C_7$-$C_{31}$ aralkyl groups, $C_3$-$C_9$ trialkylsiloxy groups, $C_8$-$C_{26}$ aryldialkylsiloxy groups, $C_{13}$-$C_{28}$ alkyldiarylsiloxy groups, and $C_{18}$-$C_{30}$ triarylsiloxy groups. More preferably, $R_{72}$, $R_{73}$, $R_{75}$, $R_{76}$, $R_{77}$, $R_{78}$, $R_{80}$, $R_{81}$, $R_{83}$, $R_{84}$, $R_{85}$, and $R_{86}$ are independently selected from the group consisting of alkyl groups (e.g., $C_1$-$C_8$ alkyl groups, haloalkyl groups (e.g., $C_1$-$C_8$ haloalkyl groups), aryl groups (e.g., $C_6$-$C_{30}$ aryl groups), and aralkyl groups (e.g., $C_7$-$C_{31}$ aralkyl groups). Most preferably, $R_{72}$, $R_{73}$, $R_{75}$, $R_{76}$, $R_{77}$, $R_{78}$, $R_{80}$, $R_{81}$, $R_{83}$, $R_{84}$, $R_{85}$, and $R_{86}$ are independently selected from the group consisting of alkyl groups (e.g., $C_1$-$C_8$ alkyl groups, preferably methyl groups). In such embodiments, $R_{74}$ and $R_{82}$ are independently selected from the group consisting of $C_1$-$C_{30}$ haloalkyl groups (e.g., $C_1$-$C_8$ haloalkyl groups), $C_7$-$C_{31}$ aralkyl groups, $C_6$-$C_{30}$ aryl groups (e.g., $C_6$-$C_{10}$ aryl groups), and $C_6$-$C_{30}$ substituted aryl groups (e.g., $C_6$-$C_{10}$ substituted aryl groups). More preferably, $R_{74}$ and $R_{82}$ are independently selected from the group consisting of $C_1$-$C_8$ haloalkyl groups, $C_6$-$C_{10}$ aryl groups, and $C_6$-$C_{10}$ substituted aryl groups. In one preferred embodiment, $R_{74}$ and $R_{82}$ are independently selected from the group consisting of $C_6$-$C_{10}$ aryl groups, with phenyl groups being particularly preferred. In another preferred embodiment, $R_{74}$ and $R_{82}$ are independently selected from the group consisting of haloalkyl groups (e.g., $C_1$-$C_8$ haloalkyl groups), with fluoroalkyl groups (e.g., $C_1$-$C_8$ fluoroalkyl groups) being particularly preferred.

As noted above, the variable c is 0 or a positive integer from 1 to 3. In a particularly preferred embodiment, c is 1.

The siloxane compound conforming to the structure of Formula (LXX) can be made by any suitable process. For example, the siloxane compound can be produced by the process described above in the second embodiment of the invention using a different set of reactants. In particular, when c is a positive integer, the first siloxane compound used in such a process preferably conforms to the structure of Formula (LXXX) and the organosilicon compound preferably conforms to the structure of Formula (XC). The structure of Formula (LXXX) is:

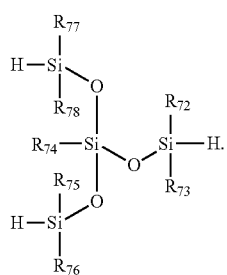
(LXXX)

In the structure of Formula (LXXX), $R_{72}$, $R_{73}$, $R_{74}$, $R_{75}$, $R_{76}$, $R_{77}$, and $R_{78}$ are selected from the groups described above in connection with the structure of Formula (LXX). The structure of Formula (XC) is:

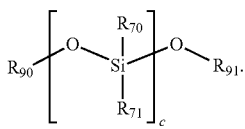
(XC)

In the structure of (XC), $R_{70}$ and $R_{71}$ are selected from the groups described above in connection with the structure of Formula (LXX). $R_{90}$ and $R_{91}$ are independently selected from the group consisting of hydrogen, alkyl groups, substituted alkyl groups, acyl groups, and substituted acyl groups. Preferably, $R_{90}$ and $R_{91}$ are independently selected from the group consisting of hydrogen, $C_1$-$C_{30}$ alkyl groups (e.g., $C_1$-$C_8$ alkyl groups or $C_1$-$C_4$ alkyl groups), and $C_1$-$C_{30}$ acyl groups (e.g., $C_1$-$C_8$ acyl groups). Most preferably, $R_{90}$ and $R_{91}$ are each hydrogen. The variable c is a positive integer, preferably a positive integer from 1 to 3, and most preferably c is 1.

As will be understood by those skilled in the art, more than one siloxane compound conforming to the structure of Formula (LXXX) can be used in the process of making the compound conforming to the structure of Formula (LXX). If more than one siloxane compound is used, the product of the process will comprise asymmetrical compounds in which the terminal cyclosiloxane groups have different substituents. Also, more than one organosilicon compound conforming to the structure of Formula (XC) can be used in the process of making the compound conforming to the structure of Formula (LXX). If more than one organosilicon compound is used, the product of the process will comprise asymmetrical compounds in which the terminal cyclosiloxane groups have different substituents. In a preferred embodiment of the compound of Formula (LXX), the compound is symmetrical as would be produced by using only one siloxane compound conforming to the structure of Formula (LXXX) and only one organosilicon compound conforming to the structure of Formula (XC).

When c is 0 in the structure of Formula (LXX), the compound can be produced by reacting a siloxane compound of Formula (CXX) with an organosilicon compound of Formula (CX). The structure of Formula (CXX) is

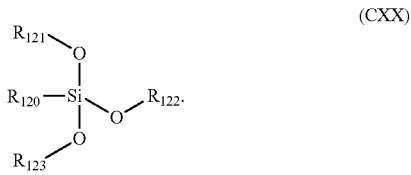
(CXX)

In the structure of Formula (CXX), $R_{120}$ is selected from the groups recited above for $R_{74}$ and $R_{82}$ when c is 0 in Formula (LXX). The structure of Formula (CX) is

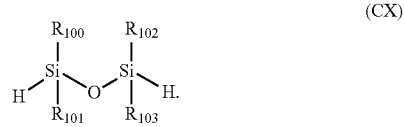
(CX)

In the structure of Formula (CX), $R_{100}$, $R_{101}$, $R_{102}$, and $R_{103}$ are selected from the groups recited above for $R_{72}$, $R_{73}$, $R_{80}$, and $R_{81}$ when c is 0 in Formula (LXX).

The compounds of Formula (LXX) in which c is 0 can also be produced with more than one siloxane compound conforming to the structure of Formula (CXX) and/or more than one organosilicon compound conforming to the structure of Formula (CX). If more than one of either of the compounds is used, the product of the process will comprise asymmetrical compounds in which the terminal cyclosiloxane groups have different substituents. In a preferred embodiment of the compound of Formula (LXX) in which c is 0, the compound is symmetrical as would be produced by using only one siloxane compound conforming to the structure of Formula (CXX) and only one organosilicon compound conforming to the structure of Formula (CX).

The siloxane compounds of the first, third, and fourth embodiments described above are believed to be suited to a variety of applications. For example, with their cyclosiloxane moieties, these siloxane compounds are believed to be well-suited for use in the production of cross-linked silicone polymers. In particular, it is believed the siloxane compounds of the first and third embodiments can be used alone or in combination with other siloxane compounds, such as a siloxane compound conforming to Formula (LXX), and reacted with a suitable ring-opening catalyst that will open the cyclosiloxane moieties and form cross-links with other siloxane compounds. The end result will be a cross-linked silicone polymer. While not wishing to be bound to any particular theory, it is believed that the siloxane compounds of the invention will have advantages over other types of siloxane compounds used in the production of cross-linked silicone polymers. For example, cross-linked silicone polymers produced by conventional condensation cure mechanisms typically release volatile organic compounds (VOCs) as they cure. These VOCs are a by-product produced by the condensation reaction that results in the formation of new Si—O—Si linkages in the curing polymer. By way of contrast, the ring-opening and cross-linking mechanism of the inventive siloxane compounds do not produce such VOCs as by-products. Further, this ring-opening curing mechanism can be initiated and propagated using relatively inexpensive materials. This stands in contrast to the relatively expensive platinum-based catalysts that are used in conventional hydrosilylation-cured cross-linked silicone polymer systems.

Thus, in a fifth embodiment, the invention provides a process for producing a cross-linked silicone polymer and a cross-linked silicone polymer produced by the process. The process generally comprises the steps of (a) providing a first siloxane compound, (b) providing a ring-opening catalyst, (c) combining the first siloxane compound and the ring-opening catalyst to produce a reaction mixture; and (d) reacting the components in the reaction mixture.

In this fifth embodiment, the first siloxane compound comprises a plurality of siloxane repeating units. Preferably, at least a portion of the siloxane repeating units are cyclosiloxane repeating units, and the cyclosiloxane repeating units are independently selected from the group consisting of cyclosiloxane repeating units conforming to the structure of Formula (XL)

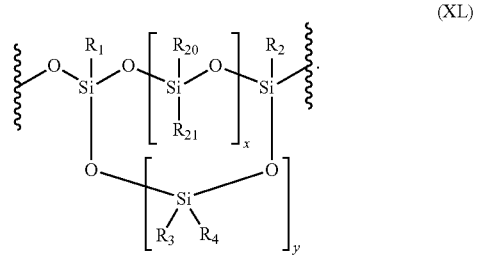

(XL)

In this embodiment, in the structure of Formula (XL), $R_1$, $R_2$, $R_3$, $R_4$, $R_{20}$, and $R_{21}$ are selected from the groups described above in connection with the siloxane compound of the first embodiment. The variable x is 0 or any positive integer; and y is a positive integer from 1 to 6. In a preferred embodiment, x is selected from the group consisting of 0, 1, and 2; y is a positive integer from 1 to 6; and the sum of x and y is an integer from 1 to 8. In a particularly preferred embodiment, at least a portion of the cyclosiloxane repeating units have a structure in which x is 0 and y is 1, which yields cyclosiloxane repeating units having a structure conforming to the structure of Formula (I). In such an embodiment, $R_1$, $R_2$, $R_3$, and $R_4$ can be selected from the groups described above in connection with Formula (I) in the siloxane compound of the first embodiment.

As with the siloxane compound of the first embodiment, the siloxane compound used in the process of this fifth embodiment can further comprise one or more segments conforming to the structure of Formula (X) described above. The siloxane compound used in the process of this fifth embodiment can also comprise one or more segments conforming to the structure of Formula (XV) described above. The siloxane compound can also comprise any suitable terminating groups, such as the various terminating groups described above in connection with the first embodiment of the invention.

As can be drawn from the foregoing discussion, siloxane compounds suitable for use in the process of this fifth embodiment include, but are not limited to, the siloxane compounds described above in connection with the first and third embodiments of the invention.

The process of this fifth embodiment of the invention uses a ring-opening catalyst to create the cross-linked silicone polymer. The ring opening catalyst can be any suitable compound that is capable of catalyzing the opening of the cyclosiloxane moieties on the first siloxane compound used in the process. Suitable catalysts are described, for example, in Chapter 1 of the book *Silicon-Containing Polymers: The Science and Technology of Their Synthesis and Applications* (James et al., Dordrecht: Kluwer Academic Publishers, 2000), in Chapter 3 of the book Handbook of *Ring-Opening Polymerization* (Dubois et al., Weinheim: WILEY-VCH Verlag GmbH & Co. KGaA, 2009), in U.S. Patent Application Publication No. 2008/0097064 A1 (Blanc-Magnard et al.), by Jaroentomeechai et al. in *Inorg. Chem.* 2012, 51, 12266-72, and by Gilbert et al. in *Journal of Polymer Science* 1959, XL, 35-58. One suitable class of ring-opening catalysts is compounds comprising one or more silanolate or siloxanolate moieties. In a preferred embodiment, the ring opening catalyst can be selected from the group consisting of siloxanolate salts (eg., tetramethylammonium siloxanolate), diaralkylsilanolate salts (e.g., sodium dimethylphenylsilanolate), and phosphonium hydroxides (e.g., tetralakylphosphonium hydroxides).

In this process embodiment, the siloxane compound and the ring-opening catalyst are combined to form a reaction mixture. The reaction mixture can comprise other components in addition to the siloxane compound and the ring-opening catalyst. For example, the reaction mixture can comprise a suitable solvent or diluent. The reaction mixture can also comprise one or more additional siloxane compounds, including siloxane compounds that are capable of participating in the curing reaction of the cross-linked silicone polymer. For example, in one embodiment, the reaction mixture can further comprise a compound conforming to a structure selected from the group consisting of Formula (LX), Formula (LXV), and Formula (LXX). The structure of Formula (LXX) is depicted above and the substituents on the structure are selected from the groups described above. The structure of Formula (LX) is

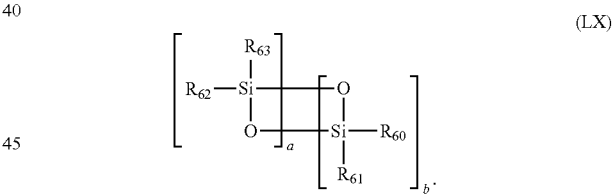

(LX)

In the structure of Formula (LX), $R_{60}$, $R_{61}$, $R_{62}$, and $R_{63}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups. The variable a is a positive integer; b is a positive integer; and the sum of a and b is from 3 to 5. Preferably, the sum of a and b is 3. Preferably, $R_{60}$, $R_{61}$, $R_{62}$, and $R_{63}$ are independently selected from the group consisting of $C_1$-$C_{30}$ alkyl groups (e.g., $C_1$-$C_8$ alkyl groups), $C_2$-$C_{30}$ alkenyl groups (e.g., $C_2$-$C_8$ alkenyl groups), $C_1$-$C_{30}$ haloalkyl groups (e.g., $C_1$-$C_8$ haloalkyl groups), $C_6$-$C_{30}$ aryl groups (e.g., $C_6$-$C_{10}$ aryl groups), $C_7$-$C_{31}$ aralkyl groups, $C_3$-$C_9$ trialkylsiloxy groups, $C_8$-$C_{26}$ aryldialkylsiloxy groups, $C_{13}$-$C_{28}$ alkyldiarylsiloxy groups, and $C_{18}$-$C_{30}$ triarylsiloxy groups. More preferably, $R_{60}$, $R_{61}$, $R_{62}$, and $R_{63}$ are independently selected from the group consisting of $C_1$-$C_8$ alkyl groups, $C_1$-$C_8$ haloalkyl groups, $C_6$-$C_{10}$ aryl groups, and $C_7$-$C_{31}$ aralkyl groups. In one specific preferred embodiment, $R_{60}$ and $R_{61}$ are selected form the group consisting of haloalkyl groups (e.g., $C_1$-$C_{30}$ haloalkyl groups, preferably $C_1$-$C_8$ haloalkyl groups), aryl groups (e.g., $C_6$-$C_{30}$ aryl groups, $C_6$-$C_{10}$ aryl groups), and aralkyl groups (e.g., $C_7$-$C_{31}$ aralkyl groups), with aryl groups being particularly preferred and phenyl groups being most preferred. In another specific preferred embodiment, $R_{62}$ and $R_{63}$ are selected from the group consisting of alkyl groups (e.g., $C_1$-$C_{30}$ alkyl groups, preferably $C_1$-$C_8$ alkyl groups), with methyl groups being particularly preferred.

The structure of Formula (LXV) is

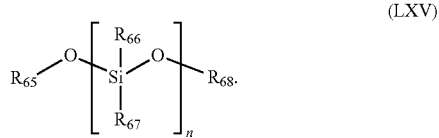

(LXV)

In the structure of Formula (LXV), $R_{65}$ and $R_{68}$ are independently selected from the group consisting of hydrogen, alkyl groups, substituted alkyl groups, acyl groups, substituted acyl groups, trialkylsilyl groups, aryldialkylsilyl groups, alkyldiarylsilyl groups, and triarylsilyl groups. $R_{66}$ and $R_{67}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups. The variable n is a positive integer. Preferably, $R_{65}$ and $R_{68}$ are independently selected from the group consisting of hydrogen, $C_1$-$C_{30}$ alkyl groups (e.g., $C_1$-$C_8$ alkyl groups or $C_1$-$C_4$ alkyl groups), and $C_1$-$C_{30}$ acyl groups (e.g., $C_1$-$C_8$ acyl groups). Most preferably, $R_{65}$ and $R_{68}$ are each hydrogen. Preferably, $R_{66}$ and $R_{67}$ are independently selected from the group consisting of $C_1$-$C_{30}$ alkyl groups (e.g., $C_1$-$C_8$ alkyl groups), $C_2$-$C_{30}$ alkenyl groups (e.g., $C_2$-$C_8$ alkenyl groups), $C_1$-$C_{30}$ haloalkyl groups (e.g., $C_1$-$C_8$ haloalkyl groups), $C_6$-$C_{30}$ aryl groups (e.g., $C_6$-$C_{10}$ aryl groups), $C_7$-$C_{31}$ aralkyl groups, $C_3$-$C_9$ trialkylsiloxy groups, $C_8$-$C_{26}$ aryldialkylsiloxy groups, $C_{13}$-$C_{28}$ alkyldiarylsiloxy groups, and $C_{18}$-$C_{30}$ triarylsiloxy groups. More preferably, $R_{66}$ and $R_{67}$ are independently selected from the group consisting of $C_1$-$C_8$ alkyl groups, $C_1$-$C_8$ haloalkyl groups, $C_6$-$C_{10}$ aryl groups, and $C_7$-$C_{31}$ aralkyl groups.

As noted above, the ring-opening catalyst reacts with the siloxane compound to open at least a portion of the cyclosiloxane repeating units. The resulting "opened" moiety (i.e., the "opened" former cyclosiloxane repeating unit) has a reactive group on its terminal end that can form an Si—O—Si linkage by reacting with another silicon atom. Thus, when this opened moiety reacts to form an Si—O—Si linkage with another molecule of the first siloxane compound, the result is a cross-link between formerly separate siloxane molecules. As this process repeats multiple times, the end result is a cross-linked silicone polymer. In order to accelerate this curing mechanism, the reaction mixture and cross-linked silicone polymer can be heated to an elevated temperature. Further, the reaction mixture preferably is degassed to avoid the formation of bubbles in the cross-linked silicone polymer. The reaction mixture can be degassed using any suitable technique known within the art.

The cross-linked silicone polymer of the invention preferably exhibits a relatively high degree of thermal stability as evinced by a lack of or very low level of yellowing after exposure to elevated temperatures. More specifically, the cross-linked silicone polymer of the invention preferably exhibits no yellowing after exposure to a temperature of 200° C. for 1,000 hours. The cross-linked silicone polymer of the invention can be made to a variety of different hardnesses, depending upon the particular conditions used in making the polymer. For example, the cross-linked silicone polymer can be a gel or can be a solid exhibiting a Shore D hardness. The cross-linked silicone polymer of the invention can also be made to exhibit a refractive index selected from a rather wide range. The refractive index of the polymer will depend on the substituents on the siloxane compound used to produce the polymer. In particular, the cross-linked silicone polymer can exhibit a refractive index from about 1.35 to about 1.6. In a preferred embodiment, the cross-linked silicone polymer exhibits a refractive index of about 1.5 or greater or about 1.55 or greater (e.g., about 1.57 or greater).

In a sixth embodiment, the invention provides a kit for producing a cross-linked silicone polymer. The kit comprises a first part and a second part. The first part and the second part are physically isolated from each other to prevent mixing of the components contained in each part. The first part comprises the first siloxane compound described above in connection with the process for producing the cross-linked silicone polymer, as well as any of the additional siloxane compounds disclosed above as being suitable for use in such process. The second part comprises the ring-opening catalyst. Thus, when the first part and the second part are mixed, the siloxane compound and the ring-opening catalyst react to form a cross-linked silicone polymer as described above.

The first and second parts of the kit can comprise other components. For example, the first part can also comprise one or more adhesion promoters. The second part can comprise a siloxane fluid, which provides a medium in which the ring-opening catalyst can be dispersed. The first or second part can also comprise a reactive or non-reactive diluent to adjust the viscosity of the system.

The kit can be provided in any suitable form. For example, the kit can be provided in the form of two separate and distinct vessels whose contents (or a portion thereof) are removed and manually mixed when the user desires to make the cross-linked silicone polymer. Alternatively, the kit can be provided in the form of a tube having two separate chambers with each chamber holding one of the first part and the second part. Each chamber can have an outlet, and the two outlets can be located proximate to each other. Thus, when the contents in the tube are compressed, the contents of each part are expelled from their respective outlets where they mix on the target surface. Alternatively, the two outlets can feed into a nozzle that is designed to thoroughly mix the contents of each part before they exit the nozzle.

The cross-linked silicone polymer described above is believed to be suited for use in a wide range of applications. Given the fact that the elastomer does not generate the VOCs typically produced by conventional condensation cure elastomers and the capability of tailoring the elastomers refractive index through the use of certain groups on the siloxane starting materials (e.g., haloalkyl groups, aralkyl groups, aryl groups, substituted aryl groups, heteroaryl groups, or substituted aryl groups), it is believed that the elastomer is particularly suited for use in electronics, such as an encapsulant for a light emitting diode (LED). Further, it is believed that the lack of VOC generation also tends to reduce shrinkage that occurs when the polymer cures (typically shrinkage is less than 5%, preferably less than 2%), making the polymer particularly well-suited for use as a sealant or encapsulant.

In a seventh embodiment, the invention provides an LED that utilizes a cross-linked silicone polymer according to the invention (e.g., a cross-linked silicone polymer produced by the above-described process or using the above-described kit) as an encapsulant. FIG. 1 provides a simplified, schematic cross-sectional view of such an LED. The LED 100 comprises (a) a semiconductor crystal 102, (b) a cathode 104 electrically connected to the semiconductor crystal 102, (c) an anode 106 electrically connected to the semiconductor crystal 102, and (d) an encapsulant material 110 surrounding the semiconductor crystal 102. As noted above, the encapsulant material 110 comprises a cross-linked silicone polymer according to the invention.

The semiconductor crystal can be composed of any crystalline semiconductor material suitable for generating radiation (e.g., visible light) when a current is passed through the material. Suitable semiconductor crystals are well-known within the art, with crystals made from gallium nitride being among those commonly used. Further, the semiconductor crystal can be carried on any suitable support known within the art, such as silicon carbide or sapphire. Basically, the semiconductor crystal 102 comprises an n-type semiconductor material in a first region (not pictured) of the semiconductor crystal and a p-type semiconductor material in a second region (not pictured) of the semiconductor material. The boundary between the first region and the second region of the semiconductor material provides a p-n junction.

The LED 100 further comprises a cathode 104 electrically connected to the first region of the semiconductor crystal 102. The cathode can be any suitable material (e.g., metal) that is capable of carrying the electric current necessary to power the LED. As shown in FIG. 1, the semiconductor crystal 102 can be directed attached to the cathode 104 thereby providing the electrical connection to the first region. Alternatively, the cathode can be connected to the semiconductor crystal by a suitable bond wire, as discussed below in regards to the anode. The anode 106 is electrically connected to the second region of the semiconductor crystal 102. The anode can be any suitable material (e.g., metal) that is capable of carrying the electric current necessary to power the LED. As shown in FIG. 1, the anode 106 can be electrically connected to the second region of the semiconductor crystal by a suitable bond wire 108. The bond wire can be any suitable material can (e.g., metal) that is capable of carrying the electric current from the anode to the second region of the semiconductor material.

As noted above, the LED 100 further comprises an encapsulant material 110 surrounding the semiconductor crystal 102. As shown in FIG. 1, the encapsulant 110 can also surround the cathode 104 and anode 106 if the two are separate from the semiconductor crystal 102, but this is not necessary. The encapsulant material provides two basic functions. First, it protects the semiconductor crystal and the electrical connections to the crystal from damage by external forces or contaminants. Second, the encapsulant material provides a transition between the high refractive index material of the semiconductor crystal and the low refractive index air surrounding the LED. As known by those familiar with the art, the relatively large difference between the refractive index of the semiconductor crystal and the surrounding air leads to internal reflection of light within the LED. These internal reflections reduce the amount of light that escapes from the semiconductor crystal and is emitted by the LED. By providing a medium with an intermediate refractive index (i.e., a refractive index between the high refractive index of the semiconductor crystal and the refractive index of air), the encapsulant material can reduce the amount of light that is internally reflected back into the semiconductor crystal, thereby increasing the amount of light emitted by the LED.

As noted above, the encapsulant material preferably comprises a cross-linked silicone polymer according to the invention. In particular, the encapsulant material preferably comprises a cross-linked silicone polymer in which at least a portion of the functional groups present on the cross-linked silicone polymer are selected from the group consisting of haloalkyl groups, aralkyl groups, aryl groups, substituted aryl groups, heteroaryl groups, or substituted aryl groups, with haloalkyl groups, aryl groups, and aralkyl groups being particularly preferred. Processes for producing such cross-linked silicone polymers are described above. It is believed that the presence of these groups yields a cross-linked silicone polymer having a higher refractive index that will provide an improved transition and lower the amount of internal reflections back into the LED.

The encapsulant material can comprise other components in addition to the cross-linked silicone polymer of the invention. For example, the encapsulant material can further comprise phosphors, which convert some of the light generated by the semiconductor crystal to different wavelengths in order to modify the wavelengths of light emitted by the LED. Any suitable phosphor or combination of phosphors can be used. Suitable phosphors are well known within the art.

As depicted in FIG. 1, the LED 100 can further comprise a cover or lens 112 enclosing the internal components. The cover or lens can serve to further protect the internal components of the LED and can also serve to focus the light generated by the LED.

The following examples further illustrate the subject matter described above but, of course, should not be construed as in any way limiting the scope thereof.

EXAMPLE 1

This example demonstrates the preparation of a siloxane compound according to the invention comprising cyclosiloxane repeating units.

54 g diphenylsilanediol (250 mmol), 200 mg tris(pentafluorophenyl)borane (0.391 mmol), and 1000 ml xylene were added at room temperature and under argon to a three neck 2L flask equipped with a magnetic stirring bar. With vigorous stirring, a mixture of 36.45 g α,ω-bis(trimethylsiloxy)polymethylhydrosiloxane (607.5 mmol [Si—H], average Mn=1700-3200) and 18 ml xylene was slowly added over 17 hours using a syringe pump at room temperature. Gas bubbles formed during the addition. After addition, the solution was further stirred for 1 hour. Approximately 74 g neutral aluminum oxide was then added to the solution, and the mixture was allowed to stand overnight. The solution was then filtered through a fritted filter. The solvent in the filtrate was then removed under high vacuum to give a sticky white product. The sticky white product was then soaked in 200 ml ethanol for 12 hours at room temperature. The ethanol was then removed under vacuum, and a sticky gum was obtained. The gum was then dissolved in around 100 ml diethyl ether. The ether solution was then added to a stirring solution of 400 ml hexamethyldisiloxane, and a precipitate formed during addition. The solution was then decanted, and the precipitate was dried under vacuum to remove any residual solvent and give 85 g of product (~94% yield). GPC (THF, room temperature, calibrated by polystyrene): Mn=5049, PD=29.3; NMR: $^1$H NMR (ppm, CDCl$_3$) δ 7.65 (broad and multiple peaks, 4H), 7.30 (broad and multiple peaks, 6H), 0.07 (broad and multiple peaks, 6H) $^{31}$C NMR (ppm, CDCl$_3$) δ 134 (multiple peaks), 130 (multiple peaks) 128 (multiple peaks) −3 (multiple peaks) $^{29}$Si NMR (ppm, CDCl$_3$) δ 8.8 (O-TMS), −37.1 (multiple peaks, —O—SiPh$_2$—O— in D3 ring), −46 (multiple peaks, —O—SiPh$_2$—O— in non-D3 form), −56.9 (Me-SiO3- in D3 ring), −66.1 (Me-SiO3- in non-D3 ring); IR: 2956, 1592, 1429, 1269, 1227, 1122, 990, 906, 843, 773, 695.

EXAMPLE 2

This example demonstrates the preparation of a siloxane compound according to the invention comprising cyclosiloxane repeating units.

80 mg tris(pentafluorophenyl)borane (0.156 mmol) and 150 ml xylene were added under argon to a three neck flask equipped with a magnetic stirring bar. The temperature of the solution was kept at 60° C. With vigorous stirring, a mixture of 12 g α,ω-bis(trimethylsiloxy)polymethylhydrosiloxane (200 mmol [Si—H], average Mn=1700-3200), 22 g dimethoxydiphenylsilane (90 mmol) and 15 ml xylene was slowly added over 3 hours. Gas bubbles formed during the addition. After addition, the reaction was kept going for another two hours at 60° C., and 0.5 hour at 120° C. The solution was then cooled to room temperature, and 41 mg triphenylphosphine (0.156 mmol) was added. The solvent was then removed under vacuum to give around 30 g of a highly viscous liquid (~96% yield). There were around 6% (mol %) Si—H and 5% (mol %) Si—OMe leftover in the product. Mn=4109, PD=14.4; $^1$H NMR (ppm, CDCl$_3$) δ 7.60 (broad and multiple peaks, 4H), 7.25 (broad and multiple peaks, 6H), 0.00 (broad and multiple peaks, 6H $^{29}$Si NMR (ppm, CDCl$_3$) δ 10, −37, −47, −57, −67; IR 2969, 1429, 1269, 1121, 988, 904, 846, 772, 695.

EXAMPLE 3

This example demonstrates the preparation of a siloxane compound according to the invention comprising cyclosiloxane repeating units.

80 mg tris(pentafluorophenyl)borane (0.156 mmol) and 150 ml xylene were added under argon to a three neck flask equipped with a magnetic stirring bar. The temperature of the solution was kept at 60° C. With vigorous stirring, a mixture of 12 g α,ω-bis(trimethylsiloxy)polymethylhydrosiloxane (200 mmol [Si—H], average Mn=1700-3200), 12 g dimethoxydimethylsilane (100 mmol) was slowly added over 4 hours. Gas bubbles formed during the addition. After addition, the reaction was held at 60° C. for another hour. The solution was then cooled down to room temperature, and 18 g Al$_2$O$_3$ was added. The mixture was left overnight. Then, the mixture was filtered and solvent was removed under vacuum to give approximately 20 g of a clear and sticky liquid (~95% yield). There were around 6% (mol %) Si—H and 9% (mol %) Si—OMe leftover in the product. Mn=4249, PD=8.5; $^1$H NMR (ppm, CDCl$_3$) δ 0.00 (broad, 12H); $^{29}$Si NMR (ppm, CDCl$_3$) δ 8, −8, −11, −19, −21, −54, −58, −67; IR 2964, 1264, 1002, 907, 849, 760, 702.

EXAMPLE 4

This example demonstrates the preparation of a siloxane compound according to the invention comprising cyclosiloxane repeating units.

54.08 g diphenylsilanediol (250 mmol), 200 mg tris(pentafluorophenyl)borane (0.391 mmol), and 1000 ml xylene were added at room temperature and under argon to a three neck flask equipped with a magnetic stirring bar. With vigorous stirring, 68.5 g of a trimethylsiloxyl-terminated methylhyrdrosiloxane-dimethylsiloxane copolymer (500 mmol [Si—H], average Mn=680) was slowly added over 24 hours using a syringe pump. Gas bubbles formed during the addition. After addition, the reaction temperature was raised to 60° C., and stirred for 4.5 hours. IR indicated no residual Si—H. Then, 78 g neutral aluminum oxide was added to the solution. After 1 hour, the solution was filtered, and the solvent in the filtrate was removed under high vacuum to give a sticky liquid (17.5 g, ~96% yield). The refractive index of the product was 1.4965 @ 589.3 nm. Mn=3543, PD=1.9; $^1$H NMR (ppm, CDCl$_3$) δ 7.60 (broad and multiple peaks, 4H), 7.30 (broad and multiple peaks, 6H), 0.00 (broad and multiple peaks, 19H); $^{31}$C NMR (ppm, CDCl$_3$) δ 134 (multiple peaks), 130 (multiple peaks), 127 (multiple peaks), 0, (multiple peaks), −3 (multiple peaks); $^{29}$Si NMR (ppm, CDCl$_3$) δ 9, −20, −36, −47, −57, −66; IR 2962, 1429, 1262, 1006, 842, 792, 697.

EXAMPLE 5

This example demonstrates the preparation of a siloxane compound conforming to the structure of Formula (LXX).

50 ml xylene, 0.04 g tris(pentafluorophenyl)borane (0.078 mmol), and 5.4 g diphenylsialnediol (25 mmol) were added under argon to a three neck flask equipped with a magnetic stirring bar. With vigorous stirring, a mixture of 5.50 g phenyltris(dimethylsiloxy)silane (16.7 mmol) and 2.75 g xylene was slowly added to the flask at 50° C. over 3 hours. Gas bubbles formed during the addition. After addition, the reaction mixture was then heated at 50° C. until no Si—H was detected by IR (around 1 hour). The reaction mixture was then cooled to room temperature, and 9 g aluminium oxide was added. After sitting overnight at room temperature, the reaction mixture was filtered, and the solvent was removed under reduced pressure to yield a clear liquid (10.5 g, ~95% yield). MALDI-TOF confirmed the molecular weight ((M+K$^+$) calculated: 1335. found: 1335). There were two adjacent peaks in GPC results, which indicated that there are two isomers present. $^1$H NMR (ppm, CDCl$_3$) δ 7.60 (multiple peaks, 16H), 7.30 (multiple peaks, 24H), 0.08 (multiple peaks, 36H) $^{31}$C NMR (ppm, CDCl$_3$) δ 134 (multiple peaks), 130 (multiple peaks), 128 (multiple peaks), 1 (multiple peaks) $^{29}$Si NMR (ppm, CDCl$_3$) δ −17, −19, −46, −48, −79; IR 2962, 1429, 1259, 1009, 839, 797, 742, 695, 597.

EXAMPLE 6

This example demonstrates the preparation of a crosslinked silicone polymer according to the invention.

A 2 g THF solution of 0.2 g of a polycyclosiloxane according to the invention and a 2.5 g THF solution of 0.6 g 1,1-diphenyl-3,3,5,5-tetramethylcyclotrisiloxane were mixed. Then, 0.048 mg tetramethyammonium siloxanolate (60 ppm, Gelest catalog SIT7502.0) in 0.196 g THF was added to the mixture. The solution was then shaken well, and the solvent was removed under vacuum to give white solids.

The solids were then heated at 75° C. for 2 hours, 125° C. for 18 hours and 150° C. for 2 hours to fully cure. The resulting cross-linked silicone polymer had a Shore A hardness of around 39 and a transparency of 97% at 400 nm.

EXAMPLE 7

This example demonstrates the preparation of different cross-linked silicone polymers according to the invention and the different properties exhibited by these polymers.

Four cross-linked silicone polymers (Samples 7A-7D) were prepared in accordance with the general procedure outlined in Example 6, with the ratio of the polycyclosiloxane compound and, if present, 1,1-diphenyl-3,3,5,5-tetramethylcyclotrisiloxane being varied as set forth in Table 1. Table 1 also lists the hardness of the resulting polymers.

TABLE 1

Reactants used to make and hardness of Samples 7A-7D.

| Sample | Weight ratio polycyclosiloxane:1,1-diphenyl-3,3,5,5-tetramethylcyclotrisiloxane | Shore Hardness |
| --- | --- | --- |
| 7A | 1:0 | >100 (A) |
| 7B | 1:1.5 | 80 (A) |
| 7C | 1:3 | 30 (A) |
| 7D | 1:6 | 16 (A) |

EXAMPLE 8

This example demonstrates the preparation of a cross-linked silicone polymer according to the invention.

0.5 g of the poly(cyclo)siloxane of Example 1 and 1.5 g phenylmethyl cyclotetrasiloxanes were dissolved in THF. Then, 0.12 mg tetramethyammonium siloxanolate (60 ppm, Gelest catalog SIT7502.0) in THF was added to the mixture. The solution was shaken well, and the solvent was removed under vacuum to give a clear liquid. The liquid was then heated at 125° C. for 16 hours to cure into a soft elastomer. The resulting elastomer had a Shore A hardness of around 20.

EXAMPLE 9

This example demonstrates the preparation of a cross-linked silicone polymer according to the invention.

0.05 g of the poly(cyclo)siloxane of Example 1 and 0.15 g phenylmethyl cyclotetrasiloxanes (Gelest catalog no SIP6737-100 g) were dissolved in THF. Then, 0.012 mg sodium dimethylphenylsilanolate (60 ppm, Sigma Aldrich, catalog no 673269-1G) in THF was added to the mixture. The solution was shaken well, and the solvent was removed under vacuum to give a clear liquid. The liquid was then heated at 75° C. for 40 minutes and 150° C. for 4 hours to cure into a soft elastomer.

EXAMPLE 10

This example demonstrates the preparation of a cross-linked silicone polymer according to the invention.

Two grams of the compound from Example 5 were dissolved in THF, and then 1.2 mg tetramethyammonium siloxanolate (600 ppm, Gelest catalog SIT7502.0) was added to the solution. THF was then removed to give a clear liquid. The liquid was then heated at 75° C. for 1 hour and 120° C. for 5 hours to cure into a very soft elastomer. The catalyst was then removed by heating at 150° C. for 1 hour. The elastomer had a Shore A hardness of approximately 0. In another experiment, 0.67 g of the polycyclosiloxane of Example 1 and 1.33 g of the compound from Example 5 were cured in a similar manner to give an elastomer with a Shore A hardness of around 50.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A siloxane compound comprising a plurality of siloxane repeating units, wherein at least a first portion of the siloxane repeating units are cyclosiloxane repeating units conforming to the structure of Formula (XL)

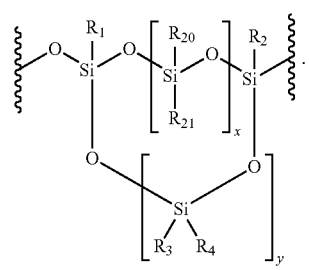

wherein R₁ and R₂ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; $R_{20}$ and $R_{21}$ are independently selected from the group consisting of hydrogen, alkyl groups, substituted alkyl groups, alkanediyl groups, substituted alkanediyl groups, cycloalkyl groups, substituted cycloalkyl groups, alkenyl groups, substituted alkenyl groups, alkenediyl groups, substituted alkenediyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; provided only one of $R_{20}$ and $R_{21}$ can be hydrogen; and further provided, if one of $R_{20}$ and $R_{21}$ is selected from the group consisting of alkanediyl groups, substituted alkanediyl groups, alkenediyl groups, and substituted alkenediyl groups, then the other of $R_{20}$ and $R_{21}$ is also selected from the group consisting of alkanediyl groups, substituted alkanediyl groups, alkenediyl groups, and substituted alkenediyl groups, and $R_{20}$ and $R_{21}$ are bonded to form a cyclic moiety; $R_3$ and $R_4$ are independently selected from the group consisting of haloalkyl groups, aralkyl groups, aryl groups, substituted aryl groups, heteroaryl groups, and substituted heteroaryl groups; x is 0 or any positive integer; and y is a positive integer from 1 to 6; and wherein at least a second portion of the siloxane repeating units are siloxane repeating units conforming to the structure of Formula (XV)

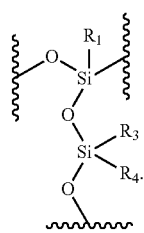

(XV)

2. The siloxane compound of claim 1, wherein the R₃ and R₄ are independently selected from the group consisting of haloalkyl groups, and aryl groups.

3. The siloxane compound of claim 2, wherein R₃ and R₄ are independently selected form the group consisting of aryl groups.

4. The siloxane compound of claim 3, wherein R₃ and R₄ are phenyl groups.

5. The siloxane compound of claim 2, wherein R₃ and R₄ are independently selected from the group consisting of haloalkyl groups.

6. The siloxane compound of claim 5, wherein R₃ and R₄ are independently selected from the group consisting of fluoroalkyl groups.

7. The siloxane compound of claim 1, wherein the siloxane compound further comprises at least one segment conforming to the structure of Formula (X)

(X)

wherein $R_{10}$ and $R_{11}$ are independently selected from the group consisting of hydrogen, alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, trialkylsiloxy groups, aryldialkylsiloxy groups, alkyldiarylsiloxy groups, and triarylsiloxy groups; provided only one of $R_{10}$ and $R_{11}$ can be hydrogen.

8. The siloxane compound of claim 1, wherein R₁ and R₂ are independently selected from the group consisting of alkyl groups and aryl groups.

9. The siloxane compound of claim 8, wherein R₁ and R₂ are independently selected from the group consisting of alkyl groups.

10. The siloxane compound of claim 9, wherein R₁ and R₂ are methyl groups.

11. The siloxane compound of claim 1, wherein the siloxane compound further comprises silyl terminating groups.

12. The siloxane compound of claim 1, wherein x is 0, 1, or 2.

13. The siloxane compound of claim 12, wherein x is 0.

14. The siloxane compound of claim 1, wherein y is 1, 2, or 3.

15. The siloxane compound of claim 14, wherein y is 1.

16. The siloxane compound of claim 1, wherein x is 0 and y is 1.

* * * * *